(12) United States Patent
Van Ingelgem et al.

(10) Patent No.: US 7,967,803 B2
(45) Date of Patent: Jun. 28, 2011

(54) TAMPON WITH RIBS HAVING A MEDIAN DIVERGING FROM THE RADIUS

(75) Inventors: Werner Van Ingelgem, Buggemmout (BE); Annelies De Geest, Aalst (BE); Djamila Mahlous, Vilvoorde (BE); Annick De Poorter, Laarne (BE); Steven Smet, Ghent (BE)

(73) Assignee: Ontex Hygieneartikel Deutschland GmbH, Grosspostwitz (DE)

( * ) Notice: Subject to any disclaimer, the term of this patent is extended or adjusted under 35 U.S.C. 154(b) by 0 days.

(21) Appl. No.: 11/021,671

(22) Filed: Dec. 22, 2004

(65) Prior Publication Data

US 2005/0193536 A1    Sep. 8, 2005

(30) Foreign Application Priority Data

Dec. 22, 2003 (EP) .................................. 03447303

(51) Int. Cl.
*A61F 13/22* (2006.01)
(52) U.S. Cl. ..................... 604/385.17; 28/118
(58) Field of Classification Search ............... 604/904, 604/385.17–385.18; 28/118–120
See application file for complete search history.

(56) References Cited

U.S. PATENT DOCUMENTS

| | | | | |
|---|---|---|---|---|
| 1,731,665 A | * | 10/1929 | Huebsch | 604/375 |
| 1,941,717 A | * | 1/1934 | Rabell | 604/377 |
| 2,263,909 A | * | 11/1941 | Webb | 28/120 |
| 2,425,004 A | * | 8/1947 | Rabell | 28/118 |
| 2,444,528 A | * | 7/1948 | Popper et al. | 604/385.17 |
| 2,499,414 A | * | 3/1950 | Rabell | 604/377 |
| 2,652,056 A | * | 9/1953 | Lay | 604/365 |
| 2,706,986 A | * | 4/1955 | Carrier | 604/385.17 |
| 2,965,101 A | * | 12/1960 | Schirmer et al. | 604/385.18 |
| 3,011,495 A | * | 12/1961 | Brecht | 604/377 |
| 3,013,558 A | * | 12/1961 | Leupold | 604/377 |
| 3,138,159 A | * | 6/1964 | Schmidt | 604/385.18 |
| 3,196,873 A | * | 7/1965 | Bletzinger et al. | 604/15 |
| 3,397,695 A | * | 8/1968 | Voss | 604/375 |
| 3,431,909 A | * | 3/1969 | Krusko | 604/15 |
| 3,610,243 A | * | 10/1971 | Jones, Sr. | 604/375 |

(Continued)

FOREIGN PATENT DOCUMENTS

EP    0 422 660 A1    4/1991

(Continued)

OTHER PUBLICATIONS

United States Patent and Trademark Office Final Office Action for U.S. Appl. No. 11/813,970 dated Mar. 17, 2011, pp. 10.

*Primary Examiner* — Jacqueline F Stephens
*Assistant Examiner* — Paula L Craig
(74) *Attorney, Agent, or Firm* — Knobbe Martens Olson & Bear LLP

(57) ABSTRACT

The invention relates to a tampon, having essentially a cylindrical shape, which includes at least three ribs defined by grooves, characterized in that at least one rib or groove, in transverse cross-section, has a median at least partially diverging from the radius and to a process for manufacturing a tampon. The invention further relates to a press for manufacturing a tampon by pressing the absorbing material radially, with press jaws including penetrating segments for penetrating the absorbing material and pressing shoulders, characterized in that the median of at least one penetrating segment diverges from the radius of that penetrating segment.

20 Claims, 22 Drawing Sheets

U.S. PATENT DOCUMENTS

| | | | |
|---|---|---|---|
| 3,643,661 A * | 2/1972 | Crockford | 604/15 |
| 3,834,389 A * | 9/1974 | Dulle | 604/369 |
| 3,981,305 A * | 9/1976 | Ring | 604/15 |
| 4,109,354 A * | 8/1978 | Ronc | 28/119 |
| 4,294,253 A * | 10/1981 | Friese | 604/385.18 |
| 4,328,804 A * | 5/1982 | Shimatani | 604/372 |
| 4,361,151 A * | 11/1982 | Fitzgerald | 604/15 |
| 4,816,100 A * | 3/1989 | Friese | 156/191 |
| 5,165,152 A * | 11/1992 | Kramer et al. | 28/118 |
| 5,403,300 A * | 4/1995 | Howarth | 604/384 |
| 5,592,725 A | 1/1997 | Brinker | |
| 5,895,408 A | 4/1999 | Pagan | |
| 5,909,884 A * | 6/1999 | Schwankhart | 28/118 |
| 5,911,712 A * | 6/1999 | Leutwyler et al. | 604/379 |
| 6,177,608 B1 * | 1/2001 | Weinstrauch | 604/380 |
| 6,206,867 B1 * | 3/2001 | Osborn et al. | 604/385.18 |
| 6,310,269 B1 * | 10/2001 | Friese et al. | 604/379 |
| 6,358,235 B1 * | 3/2002 | Osborn et al. | 604/385.18 |
| 6,433,246 B1 * | 8/2002 | Nguyen et al. | 604/375 |
| D485,354 S | 1/2004 | Carlin et al. | |
| 6,719,743 B1 * | 4/2004 | Wada | 604/385.18 |
| 6,748,634 B2 * | 6/2004 | Nguyen et al. | 28/118 |
| 6,953,456 B2 * | 10/2005 | Fuchs et al. | 604/385.17 |
| 7,070,585 B2 * | 7/2006 | Jensen | 604/385.17 |
| 2002/0151859 A1 * | 10/2002 | Schoelling | 604/385.17 |
| 2002/0157222 A1 | 10/2002 | Friese et al. | |
| 2003/0097108 A1 * | 5/2003 | Hasse et al. | 604/379 |
| 2003/0208180 A1 | 11/2003 | Fuchs et al. | |
| 2005/0113783 A1 * | 5/2005 | Carlin et al. | 604/385.18 |
| 2005/0113787 A1 * | 5/2005 | Carlin | 604/385.18 |
| 2005/0256511 A1 * | 11/2005 | Chase et al. | 604/904 |
| 2005/0277904 A1 * | 12/2005 | Chase et al. | 604/385.18 |
| 2005/0283128 A1 * | 12/2005 | Chase et al. | 604/378 |
| 2008/0154176 A1 * | 6/2008 | Van Ingelgem et al. | 604/18 |
| 2008/0221502 A1 * | 9/2008 | Binner et al. | 604/11 |

FOREIGN PATENT DOCUMENTS

| | | |
|---|---|---|
| EP | 0 639 363 A2 | 2/1995 |
| EP | 1 108 408 A1 | 6/2001 |
| WO | WO 00 53141 A1 | 9/2000 |
| WO | WO 02 078586 A2 | 10/2002 |

* cited by examiner

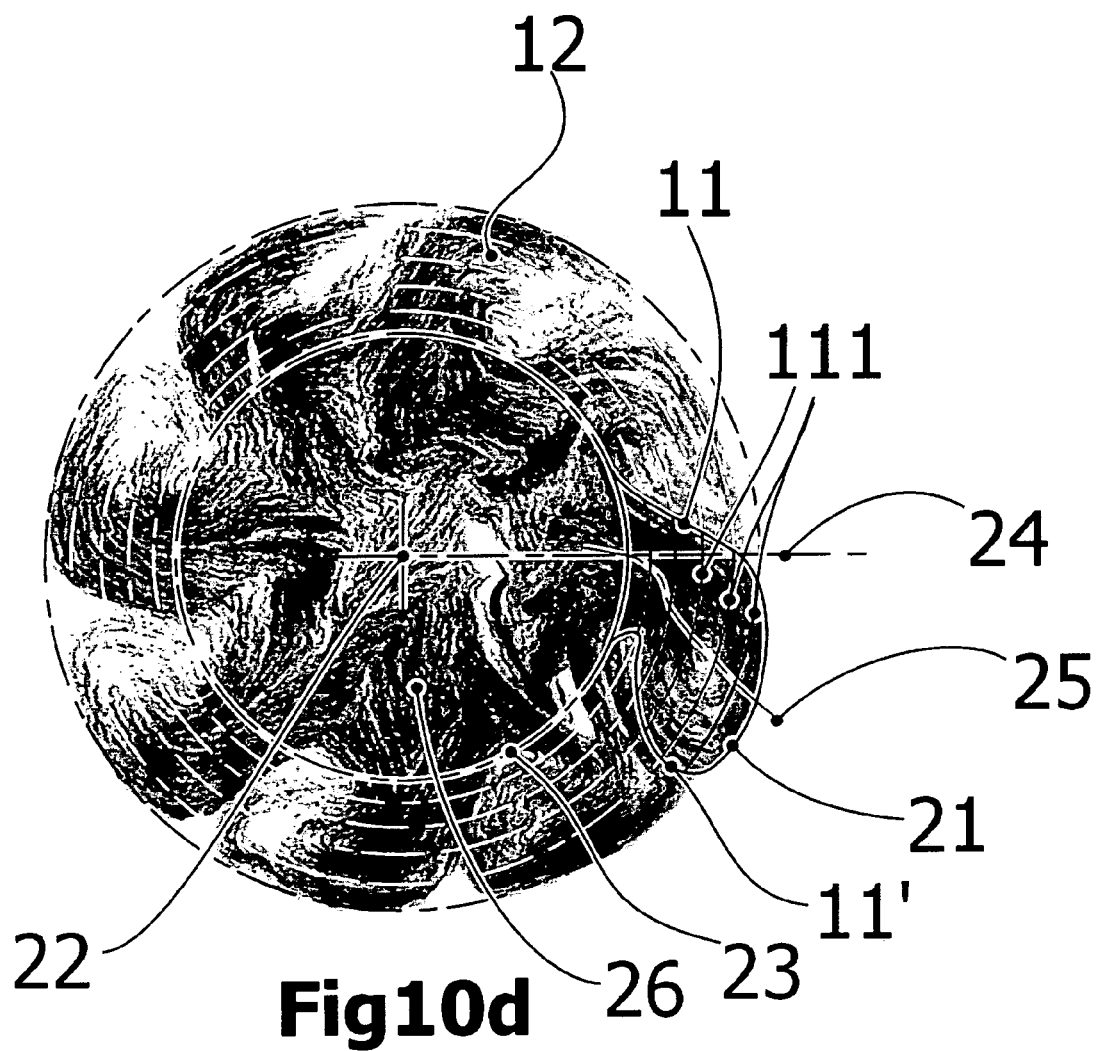

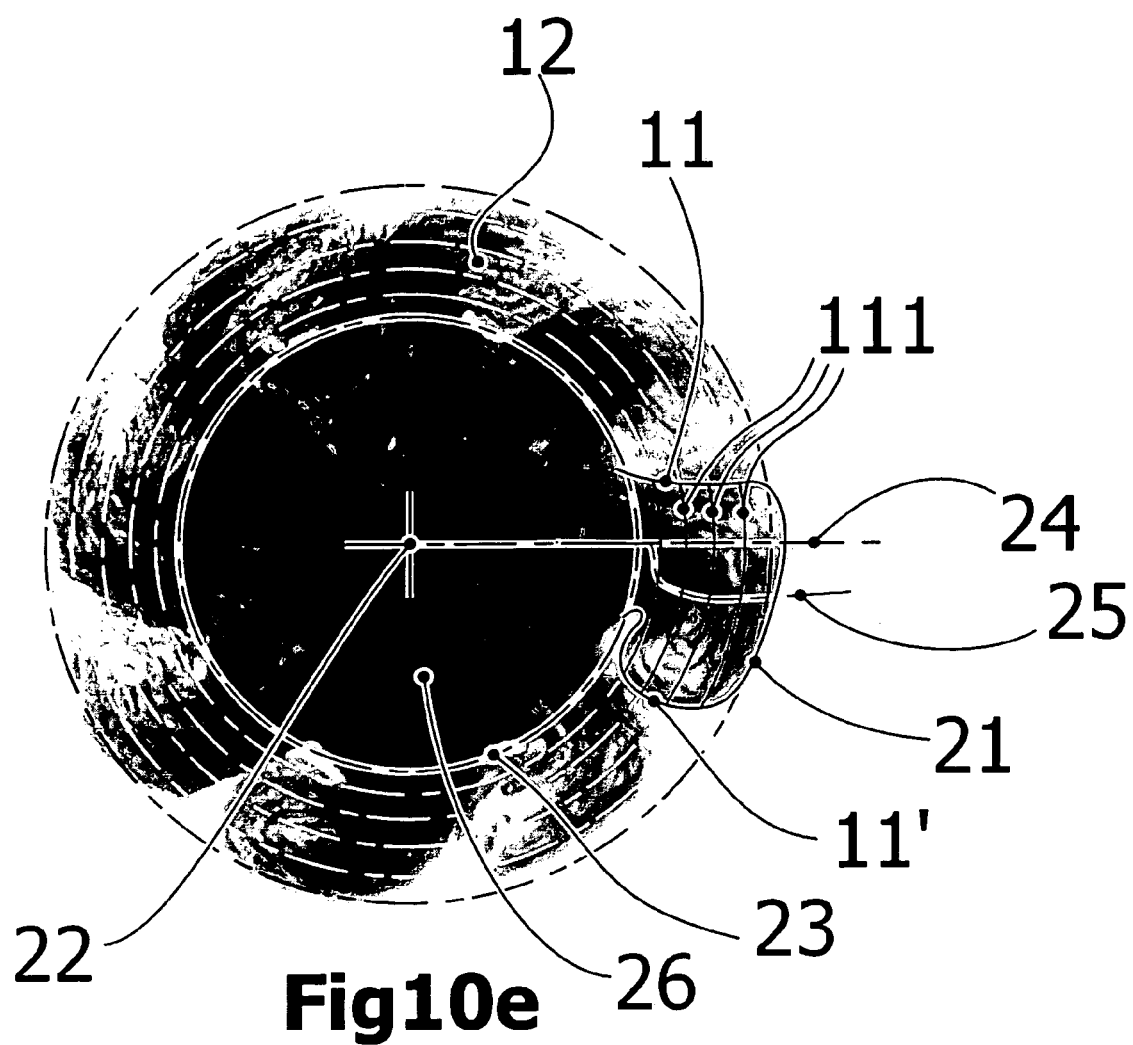

TAMPON WITH RIBS HAVING A MEDIAN DIVERGING FROM THE RADIUS

RELATED APPLICATIONS

This application claims priority to European patent application No. 03447303.3 filed on Dec. 22, 2003 which is incorporated herein by reference.

FIELD OF THE INVENTION

The invention concerns a tampon, in particular for feminine hygiene.

BACKGROUND TO THE INVENTION

From the prior art, cylindrical shaped tampons are known having ribs defined by grooves, said ribs extending radially outwards. Such tampons are known for example from WO 02/078586, EP 0 422 660, US 2002/0157222, U.S. Pat. Nos. 5,592,725, 5,895,408, EP 1 108 408, US 2003/0208180, WO 00/53141 and EP 0 639 363.

Tampons of the prior art by the nature of the design tend to have a limited absorbent and expansion capacity. Furthermore, prior to insertion into the body cavity and during use, the tampons of the prior art can feel uncomfortable.

There is a need for a new design of tampon, a device for its manufacture and a method therefore which overcomes the problems of the prior art.

AIMS OF THE INVENTION

The object of the invention is to provide a tampon with a high rate of absorption and which is comfortable in use. It is further an object of the invention to optimize the absorption and expansion by the fibers through the specific configuration of the tampon. It is further an aim of the invention to provide a tampon that is soft to the touch and therefore comfortable to insert into the body cavity. It is a further object of the invention to provide an apparatus and a method for manufacturing such tampon. A further object of the present invention is to provide an improved process for the manufacturing of a tampon and the thus obtained tampon wherein the risk for leakage is minimized.

The advantages will become clear to the persons skilled in the art from the description and the accompanying figures provided below.

BRIEF DESCRIPTION OF THE FIGURES

FIGS. 10a to 10g are schematic illustrations of cross-sections of various tampons formed according to a method or using a press of the invention, wherein FIG. 10a: the angle of the penetrating segment, beta, is 15 deg.

FIG. 10b: the angle of the penetrating segment, beta, is 15 deg.

FIG. 10c: the angle of the penetrating segment, beta, is 15 deg.

FIG. 10d: the angle of the penetrating segment, beta, is 20 deg.

FIG. 10e: the angle of the penetrating segment, beta, is 20 deg.

FIG. 10f: the angle of the penetrating segment, beta, is 30 deg.

FIG. 10g: the angle of the penetrating segment, beta, is 30 deg.

SUMMARY OF THE INVENTION

Figure 1:
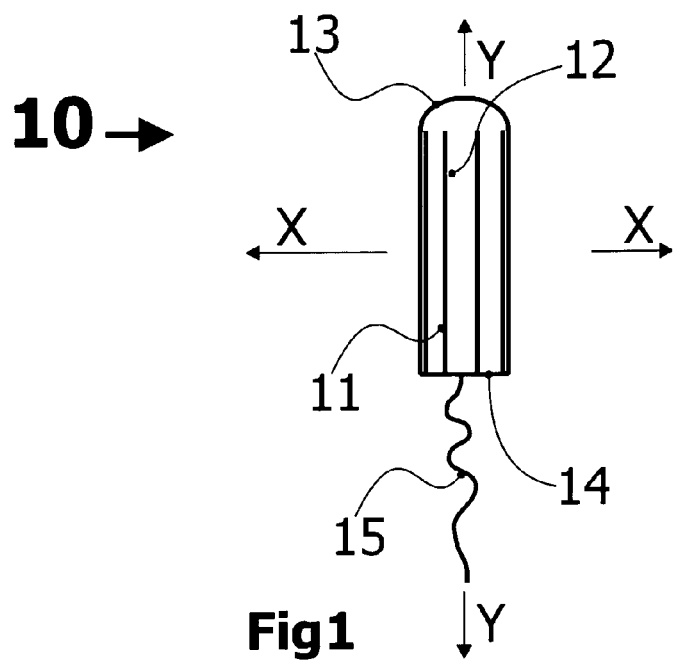
FIG. 1 is the external view of a cylindrical tampon according to the invention.

One embodiment of the present invention is a tampon, having essentially a cylindrical shape, comprising at least three ribs, characterized in that at least one rib, in transverse cross-section, has a median at least partially diverging from the radius.

Another embodiment of the present invention is a tampon as described above, in which said median of has a curved shape.

Another embodiment of the present invention is a tampon as described above, in which said median has an angular shape.

Another embodiment of the present invention is a tampon as described above, in which said median has a straight shape.

Another embodiment of the present invention is a tampon, having essentially a cylindrical shape, comprising at least three ribs defined by at least three grooves, characterized in that at least one groove, in transverse cross-section, has a median at least partially diverging from the radius.

Another embodiment of the present invention is a tampon as described above, in which said median is essentially at an angle between 1° and 60° or −1° and −60° vis à vis the radius of that rib or groove.

Another embodiment of the present invention is a tampon as described above, in which said median is essentially at an angle between 1° and 30° or −1° and −30° vis à vis the radius of that rib or groove.

Another embodiment of the present invention is a tampon as described above, in which said median is essentially at an angle between 10° and 20° or −10° and −20° vis à vis the radius of that rib or groove.

Another embodiment of the present invention is a tampon as described above, in which the tampon is provided with a finger recess.

Another embodiment of the present invention is a tampon as described above, in which the tampon is provided with a dome shaped insertion end.

Another embodiment of the present invention is a tampon as described above, in which the tampon is mushroom shaped.

Another embodiment of the present invention is a tampon as described above, in which the tampon is rivet shaped.

Another embodiment of the present invention is a tampon as described above, in which the tampon is provided with a conical shaped withdrawal end.

Another embodiment of the present invention is a tampon as described above, in which the tampon is provided with a withdrawal cord.

Another embodiment of the present invention is a tampon as described above, in which the ribs touch each other so as to form an essentially smooth cylindrical surface.

Another embodiment of the present invention is a tampon as described above, provided with one or more markings on the surface.

Another embodiment of the present invention is a tampon as described above, wherein said marking one or more of alpha numerals, graphic illustrations, patterns, solid colors and photographic illustrations.

Another embodiment of the present invention is a tampon as described above, wherein said marking is information.

Another embodiment of the present invention is a tampon as described above, provided with one or more chemical indicators that is capable of changing color.

Another embodiment of the present invention is a tampon as described above, comprising a chemical indicator that is capable of color change according to the presence of a disease or condition detectable by a color change reaction.

Another embodiment of the present invention is a tampon as described above, wherein a condition is anaemia and a chemical indicator detects iron or haemoglobin.

Another embodiment of the present invention is a tampon as described above, wherein a condition is diabetes and a chemical indicator detects glucose.

Another embodiment of the present invention is a tampon as described above, wherein a condition is a sexually transmitted disease and a chemical indicator detects antigens towards said sexually transmitted disease.

Another embodiment of the present invention is a press for manufacturing a tampon by pressing the absorbing material radially, comprising press jaws including penetrating segments for penetrating the absorbing material and pressing shoulders, characterized in that the median of at least one penetrating segment diverges from the radius of that penetrating segment.

Another embodiment of the present invention is a press as described above, wherein said penetrating segment has a median in essentially a curved shape in the direction running from the pressing head to the extreme of the penetrating segment.

Another embodiment of the present invention is a press as described above, wherein said penetrating segment has a median in essentially an angular shape in the direction running from the pressing head to the extreme of the penetrating segment.

Another embodiment of the present invention is a press as described above, wherein said penetrating segment has a median in essentially a straight shape in the direction running from the pressing head to the extreme of the penetrating segment.

Another embodiment of the present invention is a press as described above, wherein said median of the penetrating segment forms essentially an angle between 1° and 60° or −1° and −60° with the radius of the penetrating segment, to form ribs defined by grooves.

Another embodiment of the present invention is a press as described above, wherein said median of the penetrating segment forms essentially an angle between 1° and 30° or −1° and −30° with the radius of the penetrating segment, to form ribs defined by grooves.

Another embodiment of the present invention is a press as described above, wherein said median of the penetrating segment forms essentially an angle between 10° and 20° or −10° and −20° with the radius of the penetrating segment, to form ribs defined by grooves.

Another embodiment of the present invention is a press as described above, wherein the median of the penetrating segment has essentially a straight shape in the longitudinal direction.

Another embodiment of the present invention is a press as described above, wherein the median of the penetrating segment has essentially a sinusoidal shape in the longitudinal direction.

Another embodiment of the present invention is a press as described above, wherein the median of the penetrating segment has essentially a spiral shape in the longitudinal direction.

Another embodiment of the present invention is a press as described above, wherein the median of the penetrating segment has essentially a helical shape in the longitudinal direction.

Another embodiment of the present invention is a press as described above, wherein the impression depth (602, 603) varies along the longitudinal axis.

Another embodiment of the present invention is a press as described above, wherein said variation provides a profile of a tampon with a dome shape at the insertion end, in a longitudinal cross-section of a press when the press jaws are closed, so producing a tampon domed at the insertion end.

Another embodiment of the present invention is a press as described above, wherein said variation provides a mushroom-shaped profile in a longitudinal cross-section of a press when the press jaws are closed.

Another embodiment of the present invention is a press as described above, wherein said variation provides a rivet-shaped profile in a longitudinal cross-section of a press when the press jaws are closed.

Another embodiment of the present invention is a press as described above, wherein said variation provides a profile of a tampon with a conical shape at the withdrawal end, in a longitudinal cross-section of a press when the press jaws are closed, so producing a tampon with a conical shape at the withdrawal end.

Another embodiment of the present invention is a process for manufacturing a tampon, comprising:

inserting an essentially cylindrical blank of absorbing material in a press comprising press jaws including penetrating segments and pressing shoulders, pressing essentially radially the tampon blank in the press jaws, so that the penetrating segments penetrate the cylindrical blank to form ribs defined by grooves and the pressing shoulders press on the circumferential surface of the ribs so-formed, ejecting the so-formed preform, subjecting the preform to further radial pressure on its total circumference, so forming a tampon, characterized in that the median of at least one penetrating segment diverges from the radius of that penetrating segment.

Another embodiment of the present invention is a process as mentioned above, wherein said penetrating segment has a median in essentially a curved shape in the direction running from the pressing head to the extreme of the penetrating segment.

Another embodiment of the present invention is a process as mentioned above, wherein said penetrating segment has a median in essentially an angular shape in the direction running from the pressing head to the extreme of the penetrating segment.

Another embodiment of the present invention is a process as mentioned above, wherein said penetrating segment has a median in essentially a straight shape in the direction running from the pressing head to the extreme of the penetrating segment.

Another embodiment of the present invention is a process as mentioned above, wherein said median of the penetrating segment forms essentially an angle between 1° and 60° or −1° and −60° with the radius of the penetrating segment.

Another embodiment of the present invention is a process as mentioned above, wherein said median of the penetrating segment forms essentially an angle between 1° and 30° and −1° and −30° with the radius of the penetrating segment.

Another embodiment of the present invention is a process as mentioned above, wherein said median of the penetrating segment forms essentially an angle between 10° and 20° or −10° and −20° with the radius of the penetrating segment.

Another embodiment of the present invention is a process as mentioned above, wherein at least one press jaw moves in a line essentially towards the press axis, and the median of the penetrating segment is divergent from said line.

Another embodiment of the present invention is a process as mentioned above, wherein at least one press jaw moves in a line divergent from the press axis, and the median of the penetrating segment is parallel to the said line.

Another embodiment of the present invention is a process as mentioned above, wherein the median of the penetrating segment has essentially a straight shape in the longitudinal direction.

Another embodiment of the present invention is a process as mentioned above, wherein the median of the penetrating segment has essentially a sinusoidal shape in the longitudinal direction.

Another embodiment of the present invention is a process as mentioned above, wherein the median of the penetrating segment has essentially a spiral shape in the longitudinal direction. Another embodiment of the present invention is a process as mentioned above, wherein the median of the penetrating segment has essentially a helical shape in the longitudinal direction.

Another embodiment of the present invention is a process as mentioned above, wherein the impression depth varies along the longitudinal axis.

Another embodiment of the present invention is a process as mentioned above, wherein said variation provides a mushroom-shaped profile in a longitudinal cross-section of a press when the press jaws are closed, so producing a mushroom-shaped tampon.

Another embodiment of the present invention is a process as mentioned above, wherein said variation provides a rivet-shaped profile in a longitudinal cross-section of a press when the press jaws are closed, so producing a rivet-shaped tampon.

Another embodiment of the present invention is a process as mentioned above, wherein said variation provides a profile of a tampon with a dome shape at the insertion end, in a longitudinal cross-section of a press when the press jaws are closed, so producing a tampon domed at the insertion end.

Another embodiment of the present invention is a process as mentioned above, wherein said variation provides a profile of a tampon with a conical shape at the withdrawal end, in a longitudinal cross-section of a press when the press jaws are closed, so producing a tampon with a conical shape at the withdrawal end.

Another embodiment of the present invention is a process for manufacturing a tampon, comprising the use of a press as described above.

Another embodiment of the present invention is a tampon manufactured according to a process as described above.

DETAILED DESCRIPTION OF THE INVENTION

The present invention relates to a tampon in particular for feminine hygiene having a longitudinal body in an essentially cylindrical shape. The tampon is divided into a number of ribs. At least one rib has a median at least partially diverging from the radius. In detail, the tampon can be provided with the features as described below.

The median of a rib, as used in the present patent application, is the line drawn through the midpoint of a series of arc lines, bound by the edges of the rib, wherein the arcs have a common centre which is the midpoint of the X-X cross-section of the tampon. The median of the rib is depicted in FIGS. 6 to 10g as item number 25, which bisects the midpoint of a series of arcs 111 drawn through the rib, bound by the edges, 11, 11', of a rib 12, said arcs having a common centre which is the midpoint 22 of the X-X cross-section of the tampon. In all the aforementioned FIGS. 6 to 10g, the median of at least one rib clearly diverges from the radius of the rib 24 according to the invention cut across the X-X axis.

Another embodiment of the present invention a tampon is described as having a longitudinal body in an essentially cylindrical shape, divided by a number of grooves, wherein at least one groove has a median at least partially diverging from the radius of the groove.

Figure 11A:
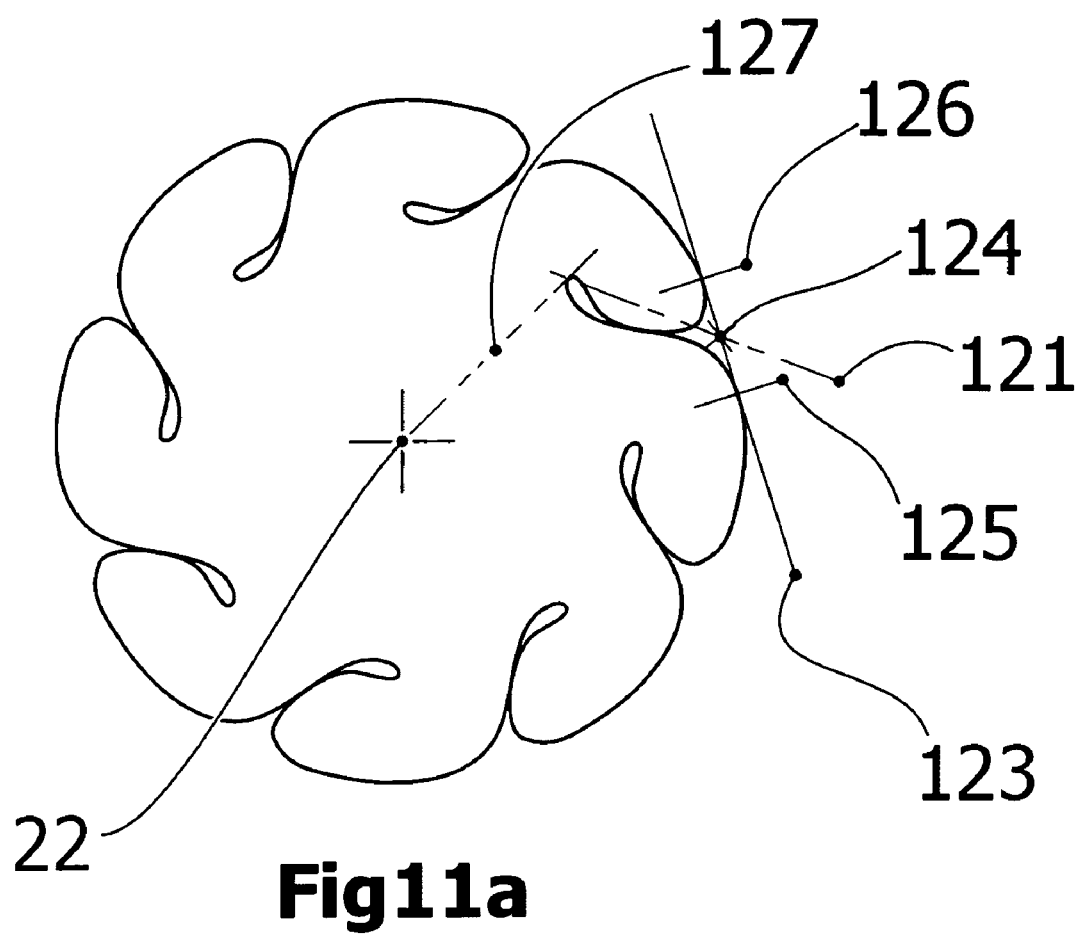
FIGS. 11a and 11b are schematic illustrations of cross-sections of various tampons formed according to a method or using a press of the invention, showing the median of the groove.
Figure 11B:
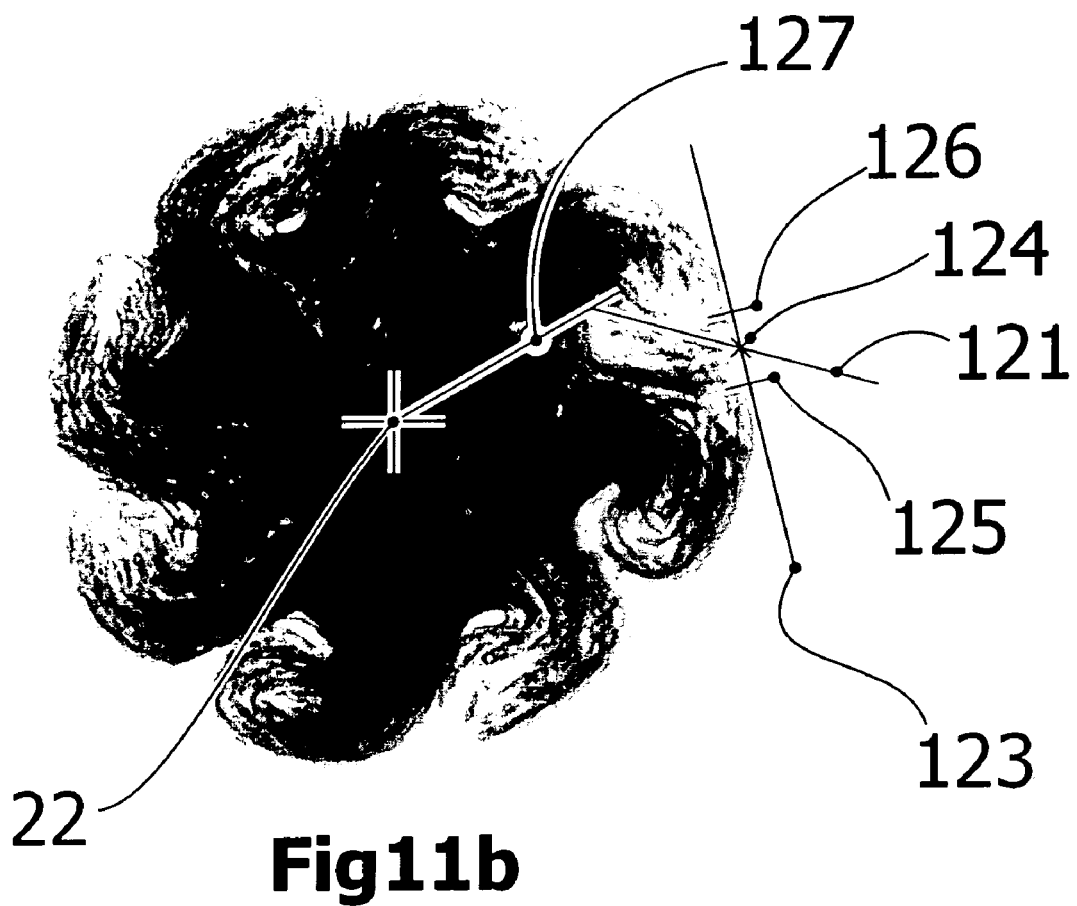

The median of a groove is the straight line that is drawn, in a cross-section of a tampon cut across the X-X axis, through the centre of the innermost point of a groove and the centre of the line drawn across the opening of the same groove, that touches the outermost circumference of the tampon either side of said groove and is bound thereby. This is illustrated in FIGS. 11a and 11b which are schematic illustrations of an X-X cross-section of a tampon according to the present invention. A median 121 of a groove is drawn from the innermost point of the groove 22 to the centre 124 of a line 123 that touches the outermost circumference of the tampon either side of said groove. The line 123 is bound by the points 125 and 126 at which it touches the outermost circumference of the tampon either side of said groove.

Absorbent fibrous material usable in the tampon according to the invention may consist of any absorbent material having acceptable absorbency and modulus of elasticity properties that is capable of absorbing and/or retaining liquid. The absorbent structure can be manufactured in a wide variety of sizes and shapes and from a wide variety of liquid-absorbing materials. It is, of course, desirable to use absorbent materials having a minimum content of extraneous soluble materials since the product may be retained in the body for a considerable period of time. Retained soluble extraneous materials could cause a safety hazard if they are toxic, irritant, or sensitive. A representative, non-limiting list of useful materials includes cellulosic materials, such as rayon, cotton, wood pulp, creped cellulose wadding, tissue wraps and laminates, peat moss, and chemically stiffened, modified, or cross-linked cellulosic fibres; synthetic materials, such as polyester fibres, polyolefin fibres, absorbent foams, e.g. a flexible resilient polyurethane foam, absorbent sponges, super-absorbent polymers, absorbent gelling materials; formed fibres, such as capillary channel fibres and multi limbed fibres; synthetic fibres, or any equivalent material or combinations of materials, or mixtures of these.

Furthermore, the present invention relates to tampons, which can be applied digitally, as well as to tampons that can be applied with an inserter and an ejector. An inserter and an ejector used to eject the tampon from the inserter after the inserter is positioned within the vagina can be any inserter known to those skilled in the art, e.g. the telescoping tube type inserters. The inserter and the ejector can be made of any of the acceptable materials, e.g. cardboard or molded polyethylene. The inserter can be sized similarly to those presently commercially used.

The tampon is at least partially provided with longitudinal ribs defined by longitudinal grooves. The longitudinal ribs can be straight, sinusoidal, spirally or helically shaped in the axial direction between the insertion end and the withdrawal end. The number of longitudinal ribs can vary, for example depending on the diameter of the tampon and/or the type of absorption material. Preferably, there are between 4 and 12 ribs, more preferably there are between 6 and 12 ribs and even more preferably, at least about eight. While the present invention, like many known tampons, may have an even number of ribs, it is also within the scope of the present invention to produce tampons with an odd number of ribs. Preferably, before use, the ribs fit closely together near the circumferential surface, providing an essentially cylindrical, smooth and soft surface. This facilitates handling of the tampon and makes insertion of the tampon more comfortable.

In cross-section, the median of the ribs can have a straight, curved, irregular or angular shape in the direction running from the circumferential surface of the tampon towards the core. It is an aspect of the invention that the median of at least one rib diverges at least partially from the radius of the rib or at least one groove diverges at least partially from the radius of the groove.

According to the invention, a median of a rib that diverges from the radius of that rib does not substantially coincide therewith for at least part of the median. For example, when the median of the rib is curved, it may, be capable of coinciding with a portion the radius of the rib towards the core of the tampon, and diverge therefrom towards the periphery of the rib. Alternatively, the median of the rib may cross the radius of the rib.

According to the invention, a median of a groove that diverges from the radius of the groove does not substantially coincide therewith for at least part of the median. For example, the median of the groove may cross the radius of the groove at angle greater than or equal to ±1, 2, 3, 4, 5, 6, 7, 8, 9, 10, 11, 12, 13, 14, 15, 16, 17, 18, 19 or 20 deg.

The inventors have found that a tampon comprising such ribs have more absorption and expansion prior to saturation. Furthermore, such a tampon is softer and more comfortable to insert.

The "radius of the rib", as used herein, refers to the straight radial line that starts at the midpoint of the X-X cross-section of the tampon and runs towards its circumference through the point where the median of the rib crosses a fictive circle formed by the internal extremes of the grooves. The radius of a rib (24) is illustrated in FIGS. 10*a* to 10*g*.

The fictive circle may also be taken to be the circle centred at the midpoint of the tampon in X-X cross-section which touches the deepest groove immediately flanking the rib. Such fictive circle (23) is illustrated on FIGS. 10*a* to 10*g*.

The "radius of the groove", as used herein, refers to the straight radial line that starts at the midpoint of the X-X cross-section of the tampon and runs towards its circumference through the point where the median of the groove crosses a fictive circle formed by the internal extremes of the grooves. The radius of a groove is illustrated in FIGS. 11*a* and 11*b* as line 127.

The fictive circle may also be taken to be the circle centred at the midpoint of the tampon in X-X cross-section that touches the groove in question.

According to one embodiment of the invention, when the median of a rib is straight said median is positioned at a minimum angle of 1, 2, 3, 4, 5, 6, 7, 8, 9, 10, 11, 12, 13, 14, 15, 16, 17, 18, 19 or 20 deg and a maximum angle of 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 deg vis à vis the radius of the rib. According to one embodiment of the invention, when the median of a rib is straight said median is positioned at a minimum angle of −1, −2, −3, −4, −5, −6, −7, −8, −9, −10, −11, −12, −13, −14, −15, −16, −17, −18, −19 or −20 deg and a maximum angle of −30, −31, −32, −33, −34, −35, −36, −37, −38, −39, −40, −41, −42, −43, −44, −45, −46, −47, −48, −49, −50, −51, −52, −53, −54, −55, −56, −57, −58, −59 or −60 deg vis à vis the radius of the rib.

According to another embodiment of the invention, when the median of a rib is straight said median is positioned essentially at an angle between 1° and 60° (or −1° and −60°) vis à vis the radius of the rib, preferably at an angle between 1° and 30° (or −1° and −30°) and more preferably at an angle between 10° and 20° (or −10° and −20°).

According to another embodiment of the invention, the median of a groove is positioned at a minimum angle of 1, 2, 3, 4, 5, 6, 7, 8, 9, 10, 11, 12, 13, 14, 15, 16, 17, 18, 19 or 20 deg and a maximum angle of 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 deg vis à vis the radius of the groove. According to another embodiment of the invention, the median of a groove is positioned at a minimum angle of −1, −2, −3, −4, −5, −6, −7, −8, −9, −10, −11, −12, −13, −14, −15, −16, −17, −18, −19 or −20 deg and a maximum angle of −30, −31, −32, −33, −34, −35, −36, −37, −38, −39, −40, −41, −42, −43, −44, −45, −46, −47, −48, −49, −50, −51, −52, −53, −54, −55, −56, −57, −58, −59, or 60 deg vis à vis the radius of the groove.

According to another embodiment of the invention, the median of a groove is positioned essentially at an angle between 1° and 60° (or −1° and 60°) vis à vis the radius of the groove, preferably at an angle between 1° and 30° (or −1 and −30°) and more preferably at an angle between 10° and 20° (or −10° and −20°).

According to the invention, when the median of all the ribs, or grooves diverge from the respective radii of the rib or groove in a regular manner, the ribs so-formed may adopt a variety of patterns in cross-section. Examples of cross-sections include, but are not limited to those indicated in the schematic drawings of FIGS. 6 to 10g. Indicated thereon are a median line 25, fictive circle 23 and radius of a rib 24. FIGS. 11a and 11b are also schematic drawings of a tampon cross-section with indicated thereon a median of a groove 121 and radius 127 of that groove. Said examples are within the scope of the present invention.

According to one aspect of the invention a rib comprises a trunk portion connected to the core of the tampon, and a rib head extending therefrom. The rib head is folded away from the trunk so producing a rib, when viewed in X-X cross-section that adopts a "P" or "b"-shape. The head of the rib may be folded in the clockwise or anticlockwise direction as depicted in FIGS. 10a to 10g.

Examples of other shapes formed by ribs include the lobe-shape, distorted trapeze shape. Other shapes include, for example, those indicated by the embodiments of the tampons of the invention according to FIGS. 6 to 9.

As a consequence of the memory effect of the fibres and the non radial position of the ribs, said ribs will fold out when receiving the first liquid. This means that the ribs will straighten towards a radial position. Tampons known from the prior art, in contrast, have ribs which expand but do not fold out. Through the unfolding of the ribs of the tampon, the expansion capacity and expansion speed of the tampon is increased. Also, the available absorption surface is increased. In addition, the relatively wide circumference also provides an important seal effect, limiting the risk of fluid by-pass and leakage.

In one embodiment, the invention provides a tampon, wherein said tampon is not covered. Preferably, tampons without covering are made from pure cotton.

In a preferred embodiment, the invention provides a tampon, wherein said tampon is at least partially surrounded by a covering. The covering is preferably not provided over the insertion end, in order to provide better access of the menses to the insertion end of the tampon. In order to improve the absorbing capacity and expansion capacity of the tampon, said covering is preferably a stretchable or elastic liquid-permeable covering. The covering can consist of, for example, a non woven covering material made of, for example, thermoplastic, heat sealing fibers or a plastic film. Such a covering improves the comfort of introduction and prevents fibres being detached during introduction or removal of the tampon into or from the body cavity.

A further preferred feature of the tampon of the invention is a withdrawal cord, extending from the withdrawal end of the tampon, in order to ease withdrawal of the tampon.

Also, the tampon is preferably provided with a round domed insertion end of high compression. This will make insertion of the tampon easier because the narrowed end goes deepest in the vagina.

Figure 1B:
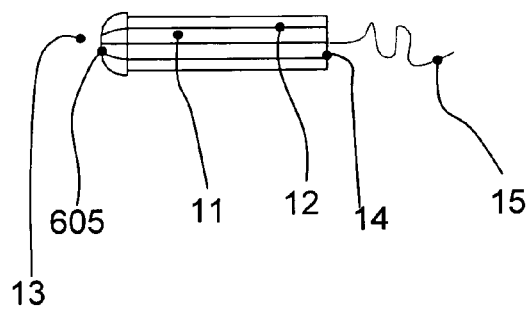
FIG. 1b is the external view of a mushroom-shaped tampon according to the invention.
Figure 1C:
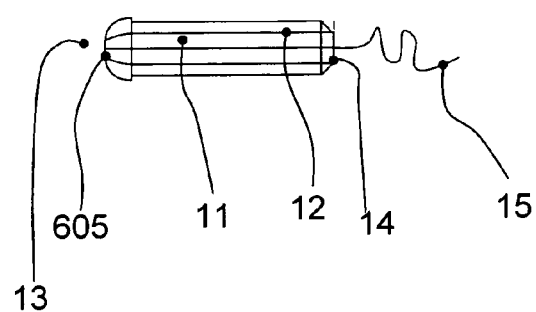
FIG. 1c is the external view of a mushroom-shaped tampon with a conical shaped withdrawal end according to the invention.
Figure 1D:
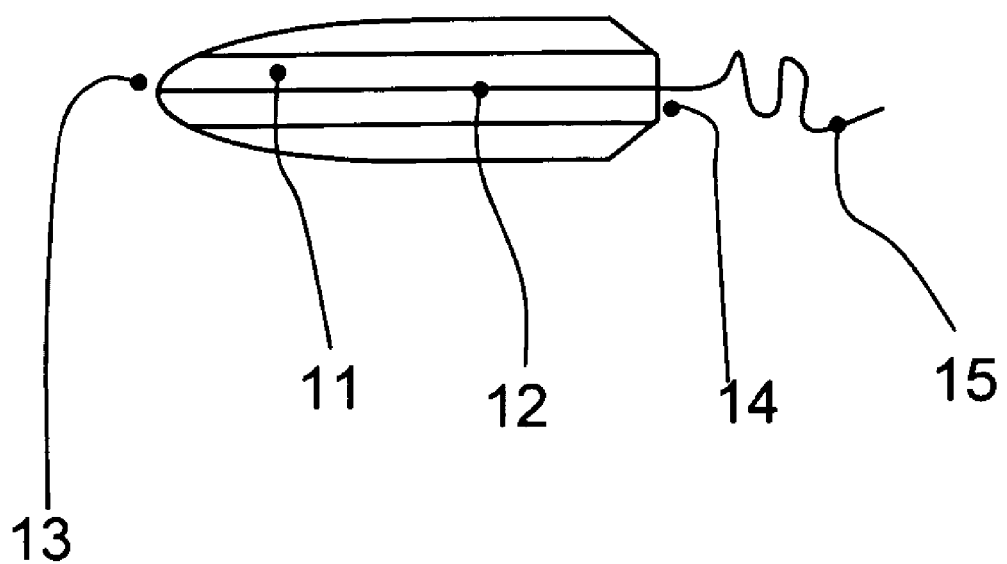
FIG. 1d is the external view of a tampon with a dome-shaped insertion end and a conical shaped withdrawal end according to the invention.

A tampon may further be provided with a conical withdrawal end (e.g. FIGS. 1c, 1d). The conical shape is one which is preferably truncated from its point. Such conical end guides the tampon during withdrawal, so making withdrawal easier.

In a further preferred embodiment, the withdrawal end is provided with a finger recess according to any technique known in the art. This facilitates the handling and the insertion of the tampon.

Figure 2:
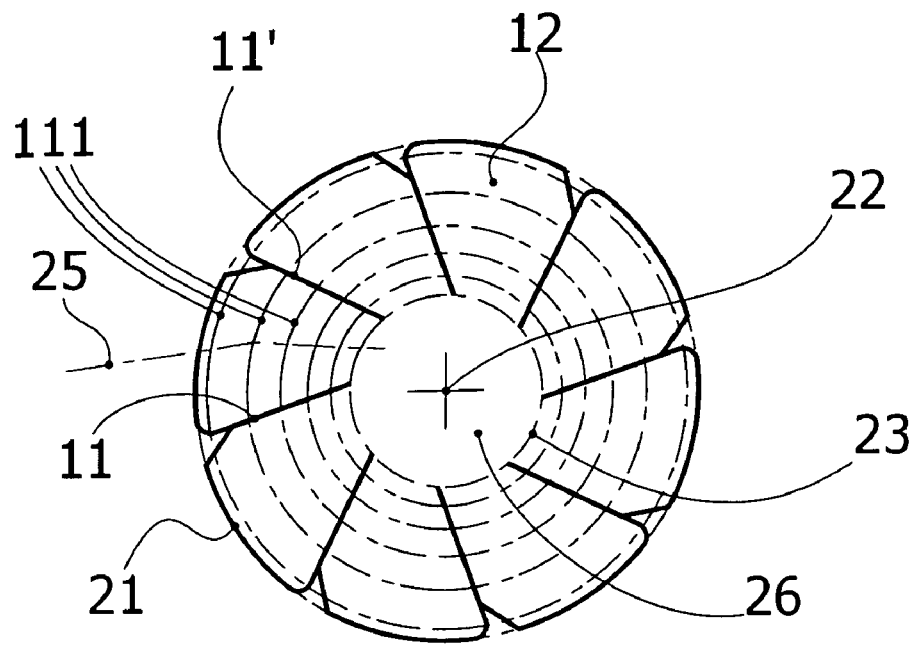
FIG. 2 shows a cross-section of the tampon of FIG. 1, cut along axis X-X.

An embodiment of the tampon of the invention is shown in FIGS. 1 and 2. FIG. 1 is the external view of a tampon according to the invention and FIG. 2 shows a cross-section of the tampon of FIG. 1 cut along axis X-X. The tampon 10 is at least partially provided with longitudinal ribs 12 defined by longitudinal grooves 11. The longitudinal ribs 12 are straight in the axial direction Y between the insertion end 13 and the withdrawal end 14. As can be seen in FIG. 2, the ribs 12 fit closely together near the circumferential surface 21, providing an essentially cylindrical and smooth surface. This facilitates handling of the tampon and makes insertion of the tampon more comfortable.

The tampon 10 has a round domed insertion end 13, to facilitate insertion of the tampon, and is further provided with a withdrawal cord 15 at the withdrawal end 14 in order to facilitate withdrawal of the tampon after use.

Figure 8:
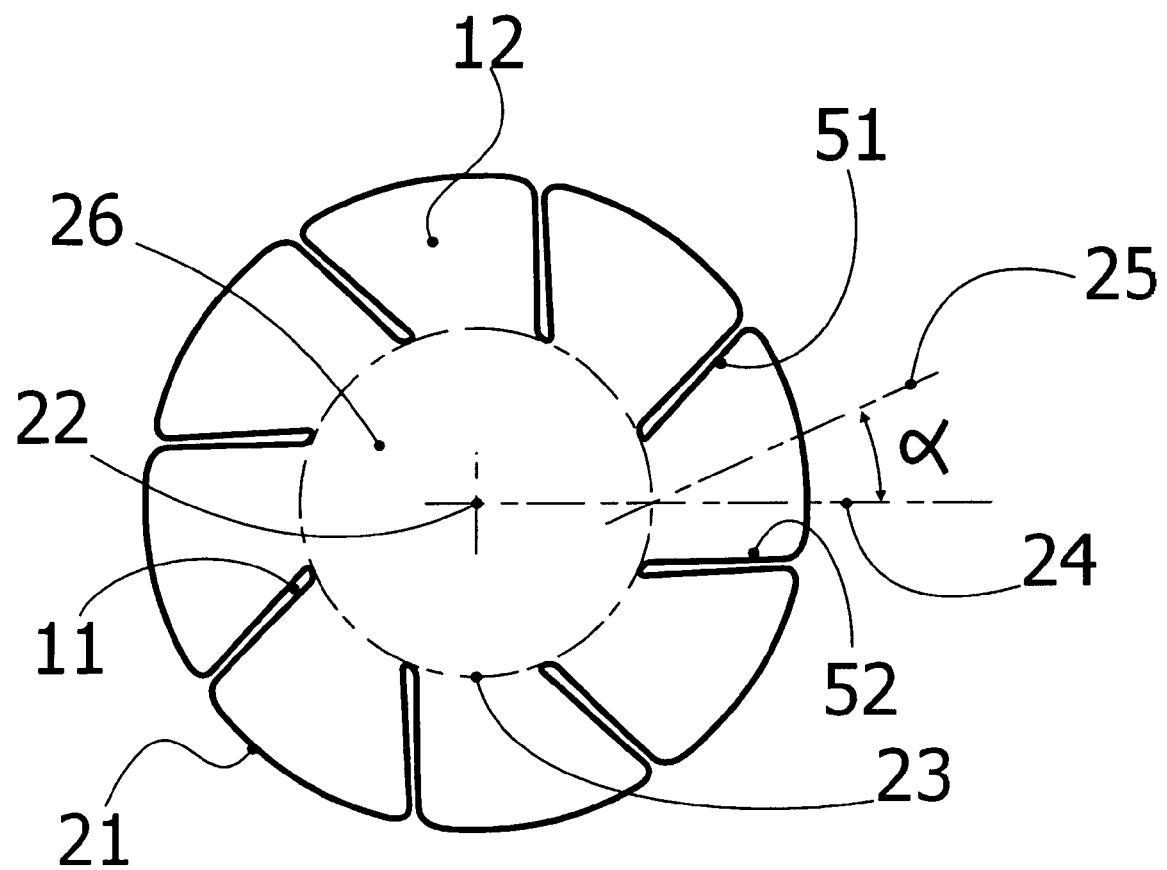
Figure 9:
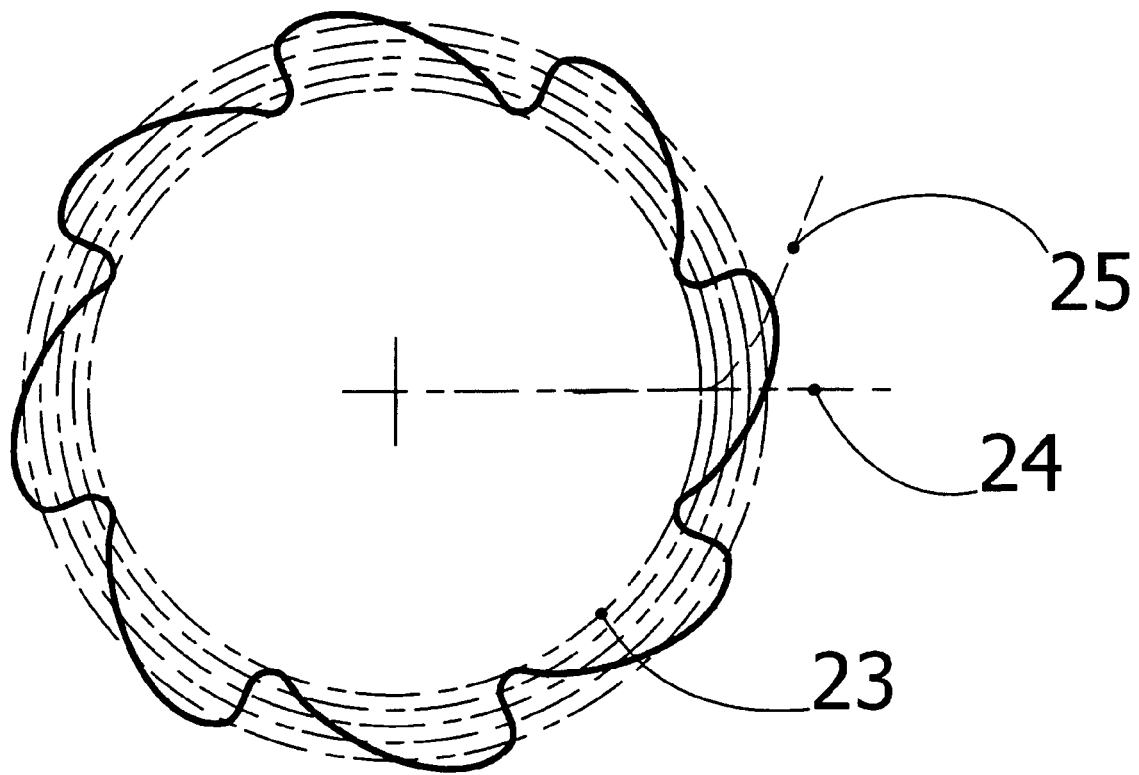
FIG. 9 illustrates a tampon according to the invention having absorbed liquid.
Figure 10A:
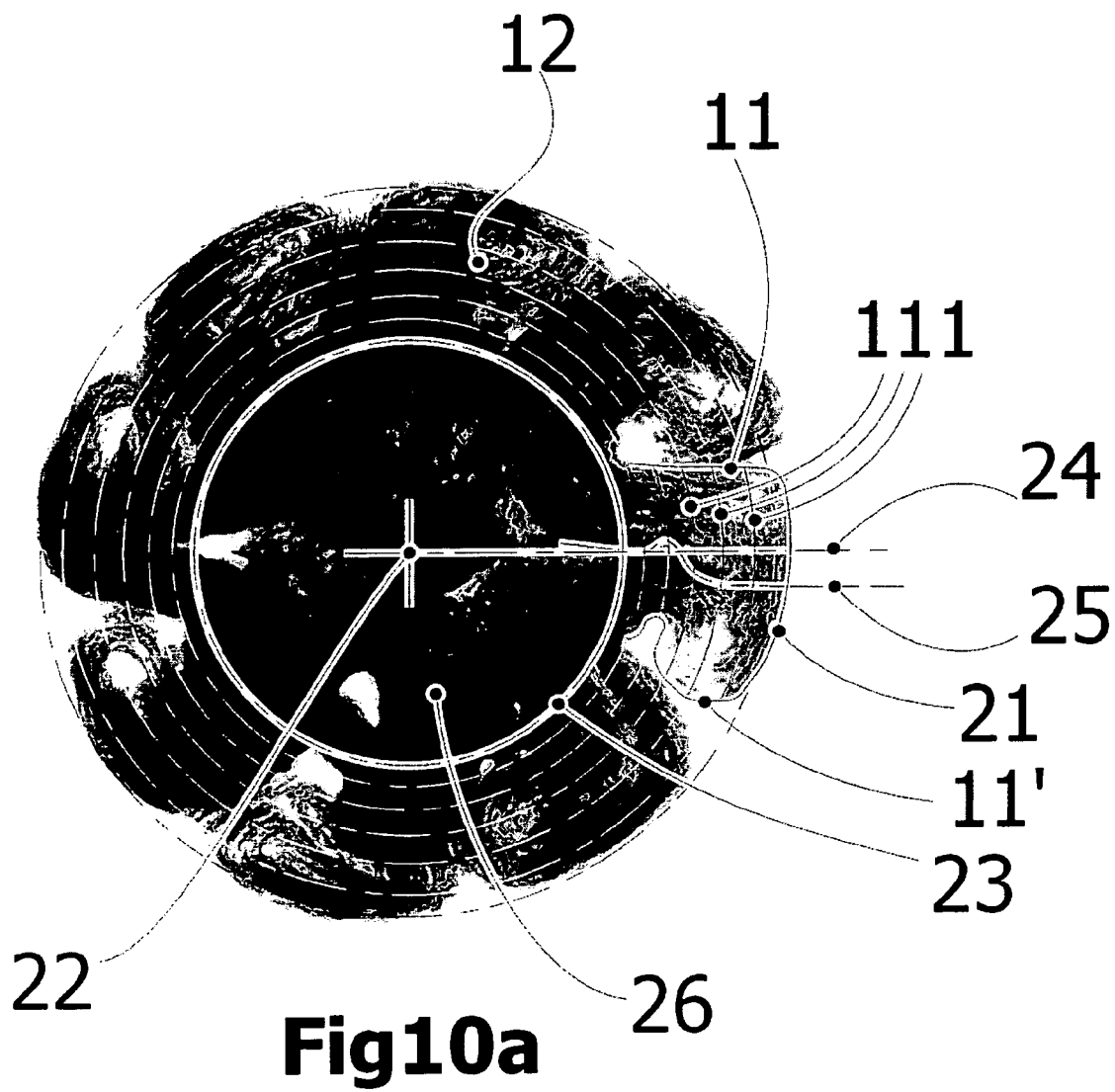
Figure 10B:
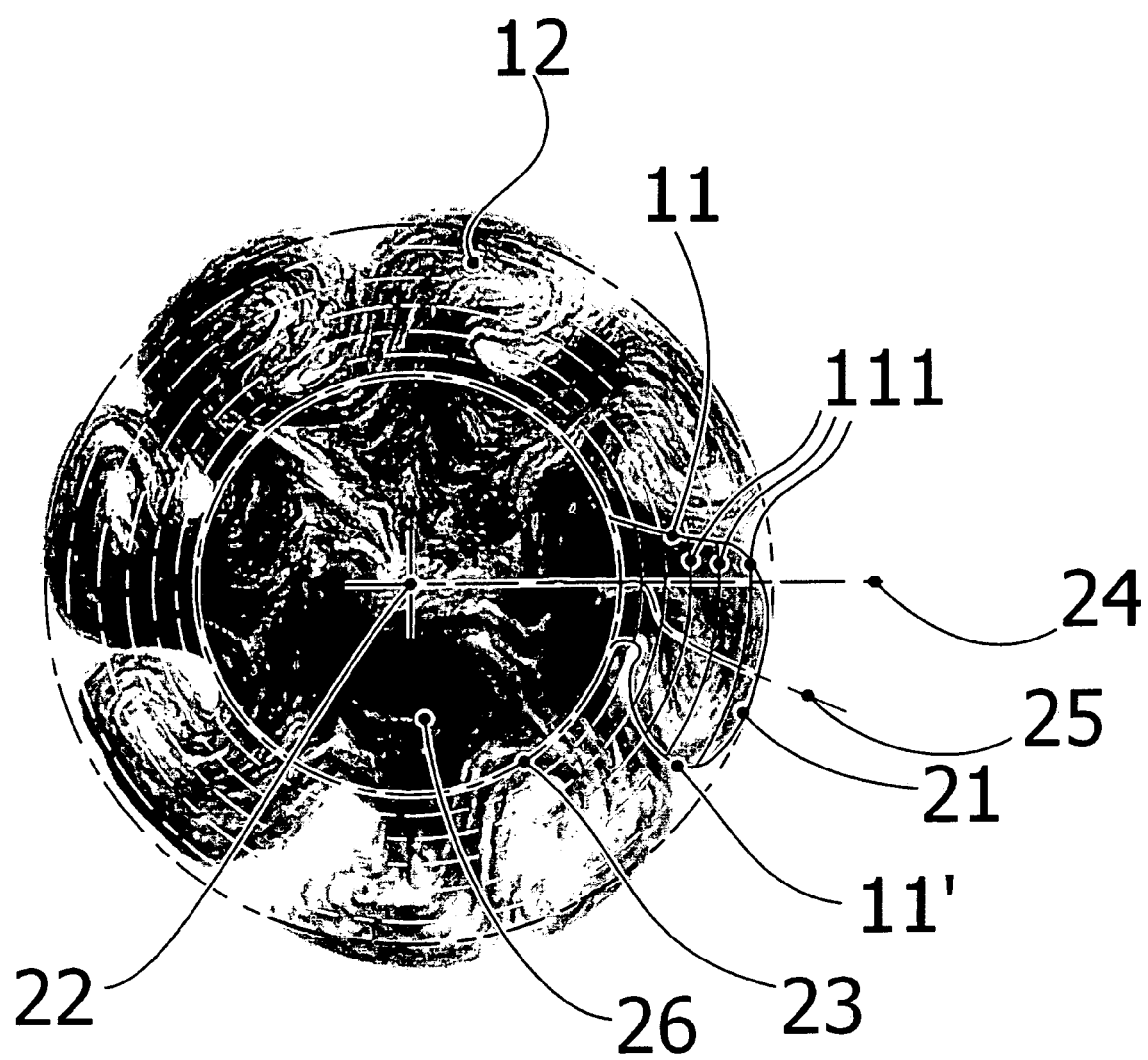
Figure 10C:
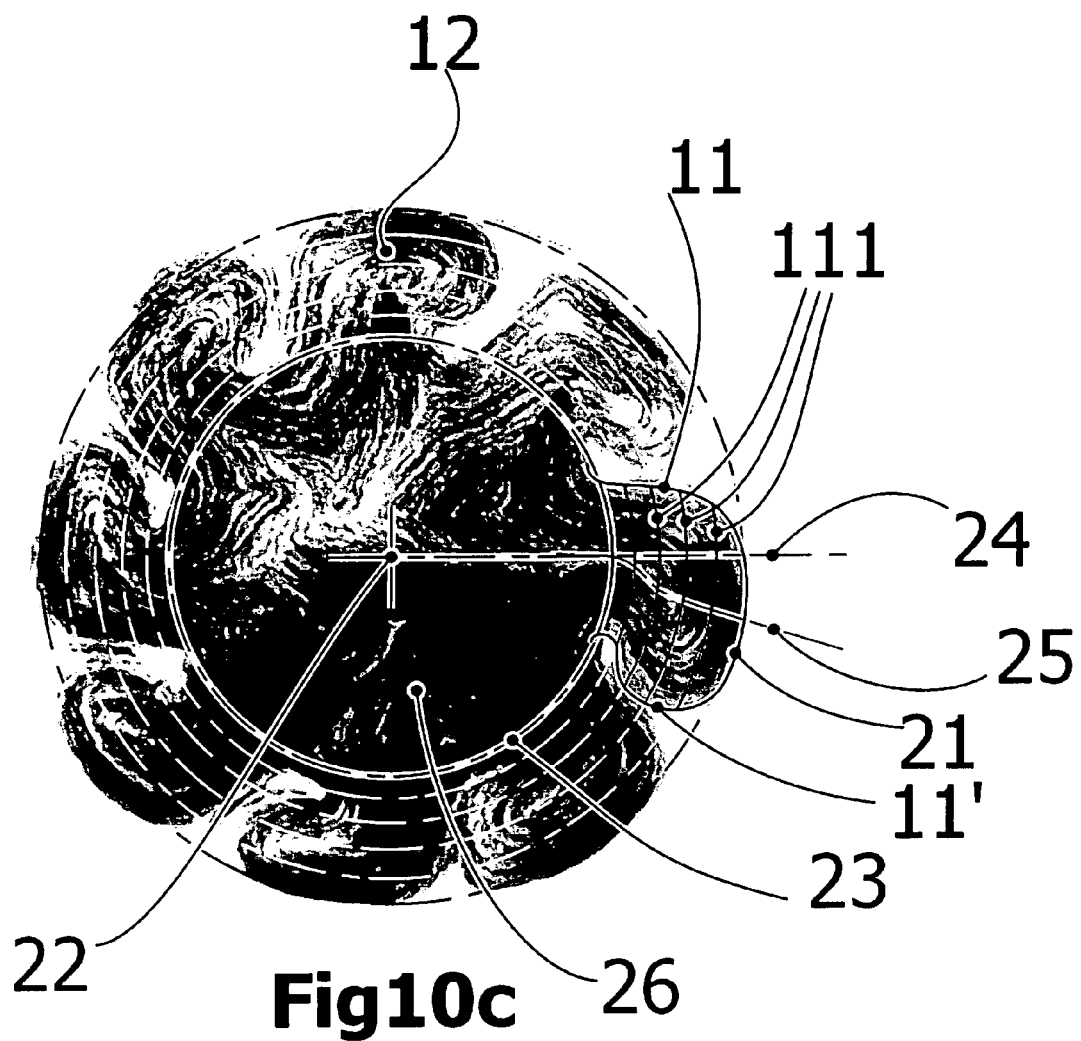
Figure 10F:
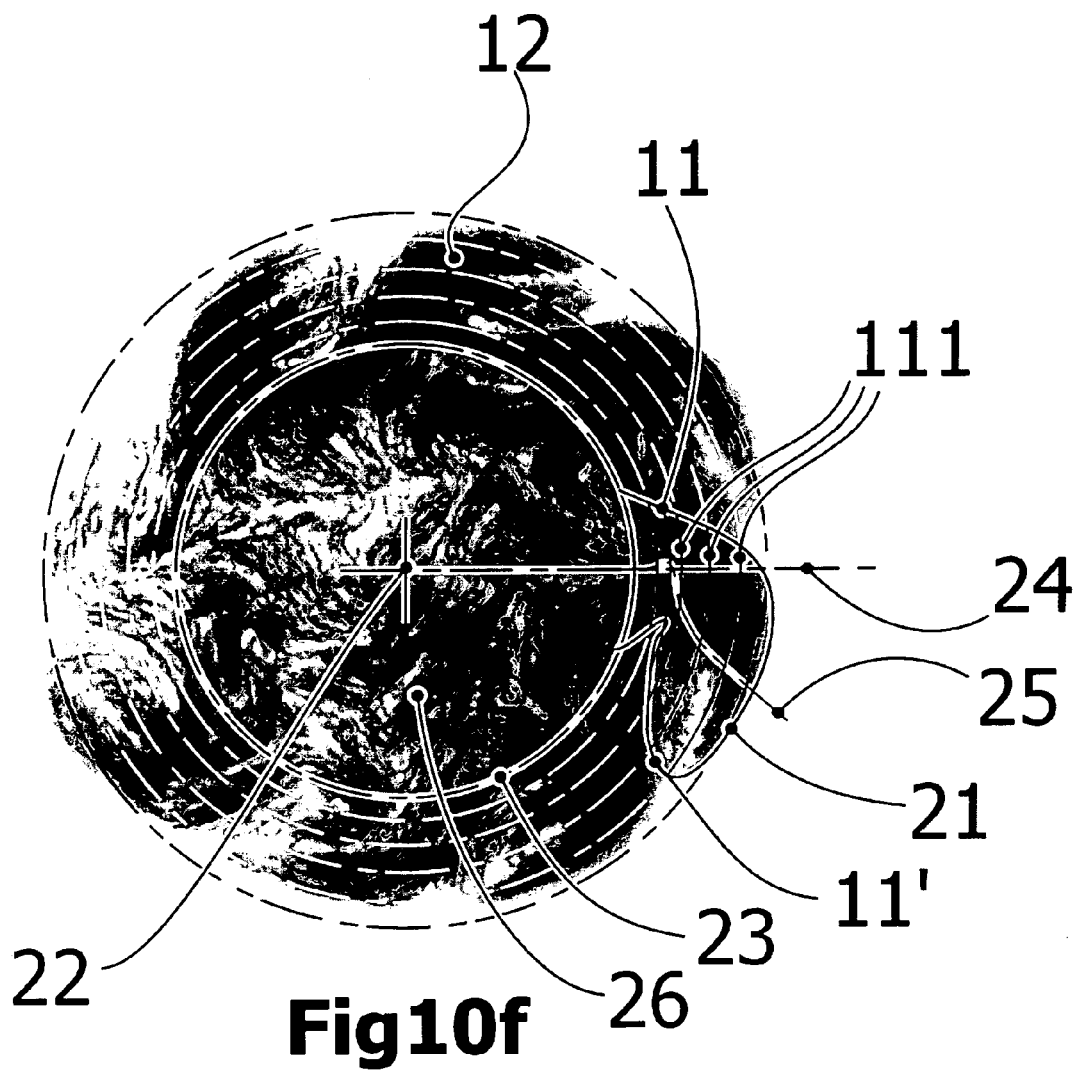
Figure 10G:
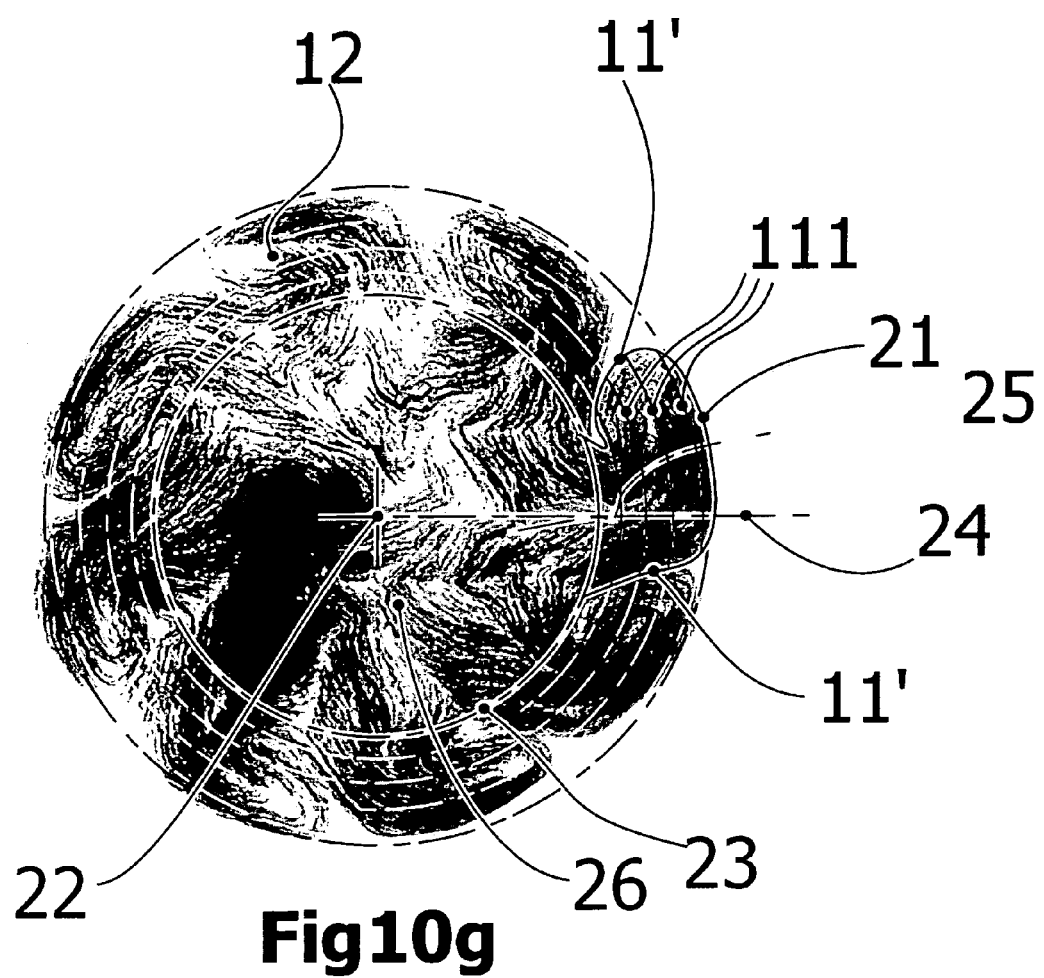

In FIG. 8, it can be seen that the median 25 of each rib 12 has a straight shape in the direction running from the circumferential surface 21 of the tampon towards the core 26. In particular, the median 25 of each rib 12 is positioned essentially at an angle $\alpha$ of about $\pm 15°$ vis à vis the radius of the rib 24. The radius of the rib that is used to determine the angle $\alpha$, is the straight radial line 24 running through the midpoint 22 of the tampon, on the one hand, and the point where the median of the rib reaches the fictive circle 23 formed by the internal extremes of the grooves 11, on the other hand.

A tampon of the invention may optionally be provided with one or more markings on the surface. A marking may be provided by any mean means including printed using inks, or by impression. A marking may comprise any features including alpha numerals, graphic illustrations, patterns and/or photographic illustration. A marking may be, for example, information such as expiry date, absorbent capacity, use instruction, warning indications. Where a tampon is provided with information, it is an information carrier. A marking may also be advertising. A marking may provide product appeal to the user or groups of users. For example, it may comprise images, patterns, graphics or alpha numerals designed to appeal to a mind set of a user group by way of aesthetic appearance and/or life-style association (e.g. cartoons, logos etc.).

A tampon of the invention may optionally be provided in one or more colors. Colors may be printed as mentioned above, or impregnated into the material. A color may indicate an expiry date, an absorbent capacity, a size or other information regarding the product. A color may be designed to appeal to a mind set of a user group by way of aesthetic appearance and/or life-style association.

It is a further aspect of the invention that a tampon is provided with chemical indicator that is capable of indicative color change. Such indicator may show, for example, a medical condition. The chemical indicator may react within one or more agents in bodily fluids to indicate an abnormality. For example, a chemical indicator may change color when a subject is suffering such as anaemia (by detecting iron/haemoglobin density), diabetes (by detecting glucose), position in the menstrual cycle (by detecting hormones), the presence of sexually transmitted diseases (by detecting antigens towards for example, gonorrhea, syphilis, hepatitis A, B or C, herpes, HIV, chlamydia) etc.

The invention also concerns an apparatus for manufacturing the tampon of the invention.

In the prior art, pressing machines have penetrating segments, which form ribs defined by grooves and which penetrate the absorbing material in essentially a radial direction, i.e. in a direction leading to the central axis of the tampon. As a result, the ribs extend radially outwards and their medians form an essentially straight line towards the central axis of the tampon. Such machines are known for example from EP 0 422 660 and EP 0 639 363.

The press apparatus of the current invention is described in detail below and exemplified by FIGS. 3*a*, 3*b*, 4*a* and 4*b*. FIG. 3*b* shows the press jaws of a press according to the invention in open position and FIG. 4*b* shows the press jaws of another press according to the invention having penetrated the cylindrical tampon blank.

The press apparatus of the current invention comprises a press having press jaws which are arranged in a star formation with respect to the press axis and preferably at the same radial distance from the press axis. They can be moved in a common plane radially with respect to the press axis between their open position and closed position and, in their closed position, are supported on one another on their mutually opposite longitudinal sides. A preferred press consists of eight press jaws. It is desirable to equip the press with an even number of press jaws, but other numbers of press jaws can be used, including odd numbers. The number of press jaws can vary, for example depending on the weight and the composition of the material intended for the tampon and can also be smaller or greater than eight, although the number generally should not be under three.

One press jaw may comprise either a penetrating segment or a pressing shoulder, or a combination of one penetrating segment and pressing shoulders arranged at either or both sides of the penetrating segment. If the penetrating segments and the pressing shoulders are fixed to separate press jaws, said penetrating segments and pressing shoulders may press separately or simultaneously. It is preferable that they press simultaneously, preferably in one single pressing operation.

The press jaws can preferably be heated and preferably each press jaw has its own temperature sensor. By heating the press jaws, it is possible to reduce the memory effect of modern, highly absorbent, greatly expanding fibrous materials, which occurs after the tampon has been finished. By means of the heated press jaws, and especially the heated pressing shoulders, the surface of the tampon is simultaneously smoothed during pressing and pushing out, and a qualitatively improved surface is produced in the preformed tampon even in tampon preforms of low weight, the stability of the tampon preform being preserved. The memory effect of the fibrous material becomes effective again when the fibrous material of the tampon is wetted with body fluid.

At least one penetrating segment penetrates the absorbing material in a line diverging from the radius. At least one penetrating segment can have a median in a straight, curved or angular shape in order to form essentially straight, curved or angular grooves into the tampon. According to one aspect of the invention, the median of a penetrating segment is the line drawn through the middle of the cross-section of a penetrating segment so that the distance from either side of the line to the edge of the penetrating segment is the same. According to another aspect of the invention, the median of a penetrating segment may be the straight line drawn, in a cross section of a penetrating segment, through its tip and the midpoint of its base.

According to one embodiment of the invention, when the medians of a penetrating segment has a straight shape, it forms a minimum angle of ±1, 2, 3, 4, 5, 6, 7, 8, 9, 10, 11, 12, 13, 14, 15, 16, 17, 18, 19 or 20 deg and a maximum angle of 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 deg vis à vis the radius of the corresponding penetrating segment.

According to another embodiment of the invention, when a median of a penetrating segment has a straight shape, it forms an angle between 1° and 60° (or −1° and −60°) vis à vis the radius of the corresponding penetrating segment, preferably an angle between 1° and 30° (or −1° and −30°) and more preferably an angle between 10° and 20° (or −10° and −20°). The "radius of the penetrating segment" (59), as used herein, refers to the radius of the fictive circle formed by the extremes of the penetrating segments, which runs through the point where the median of the corresponding penetrating segment crosses the fictive circle.

The pressing shoulders can be straight or angular, but preferably have a curvature in the transversal direction in order to press the circumferential surface of the tampon blank into an essentially cylindrical form of smaller diameter.

The press jaws and in particular the penetrating segments can have a straight, sinusoidal, spiral or helical shape in the longitudinal direction, to form essentially straight, sinusoidal, spiral or helical grooves in the axial direction of the tampon.

Figure 3A:
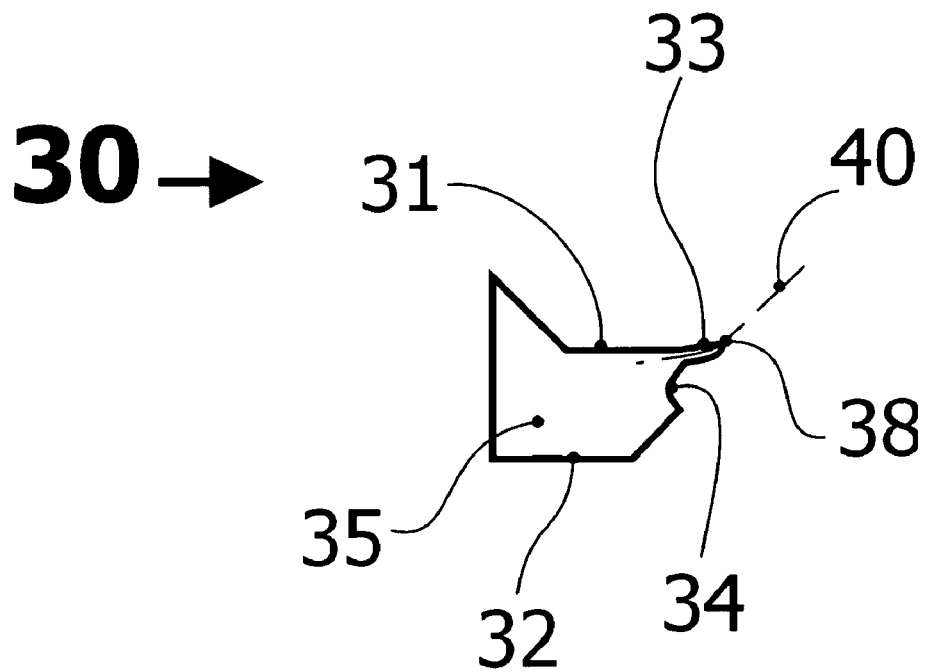
FIG. 3a shows a single press jaw according to the invention, having an angular pressing shoulder.
Figure 3B:
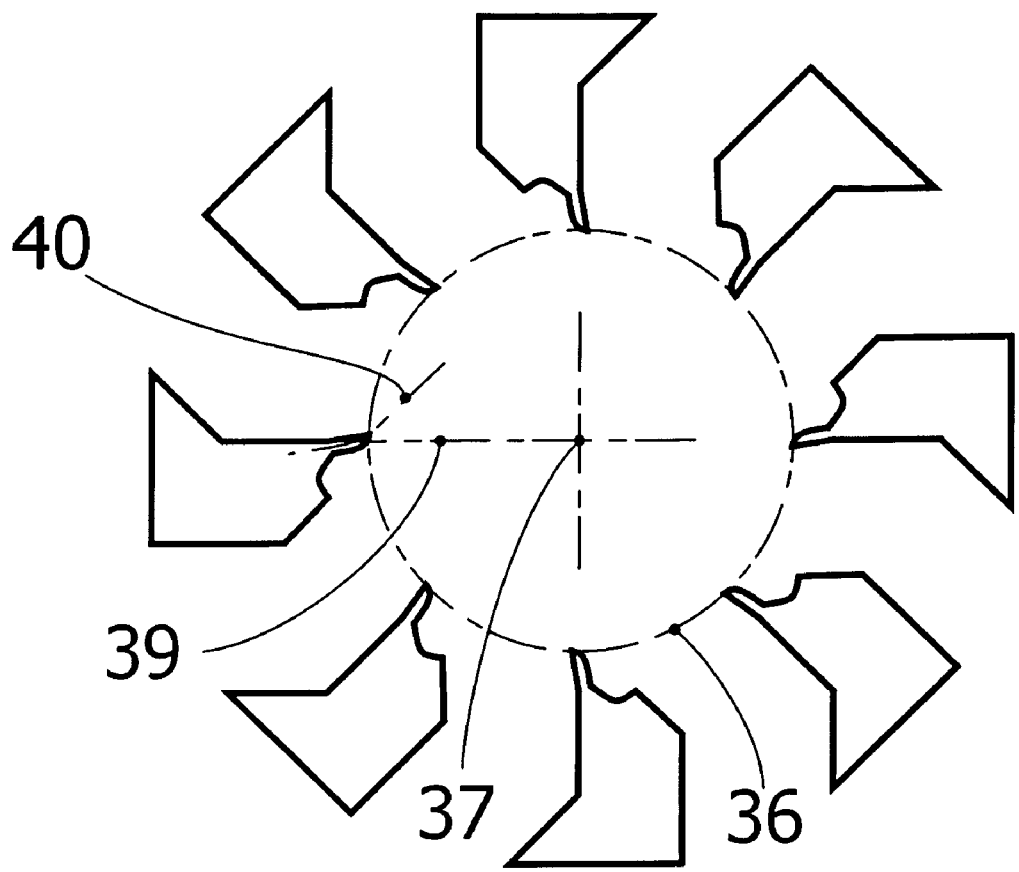
FIG. 3b shows a set of press jaws of FIG. 3a in a press according to the invention in an open position.

FIGS. 3*a* and 3*b* show an embodiment of the press jaws of a press according to the current invention. The press jaws 30 are arranged in a star formation with respect to the press axis 37 and in particular at the same radial distance from the press axis 37. They can be moved in a common plane radially with respect to the press axis 37 between their open position and closed position and, in their closed position, are supported on one another on their mutually opposite longitudinal sides 31 and 32. The press is equipped with eight press jaws 30.

One press jaw 30 combines one penetrating segment 33 and one pressing shoulder 34.

Figure 4A:
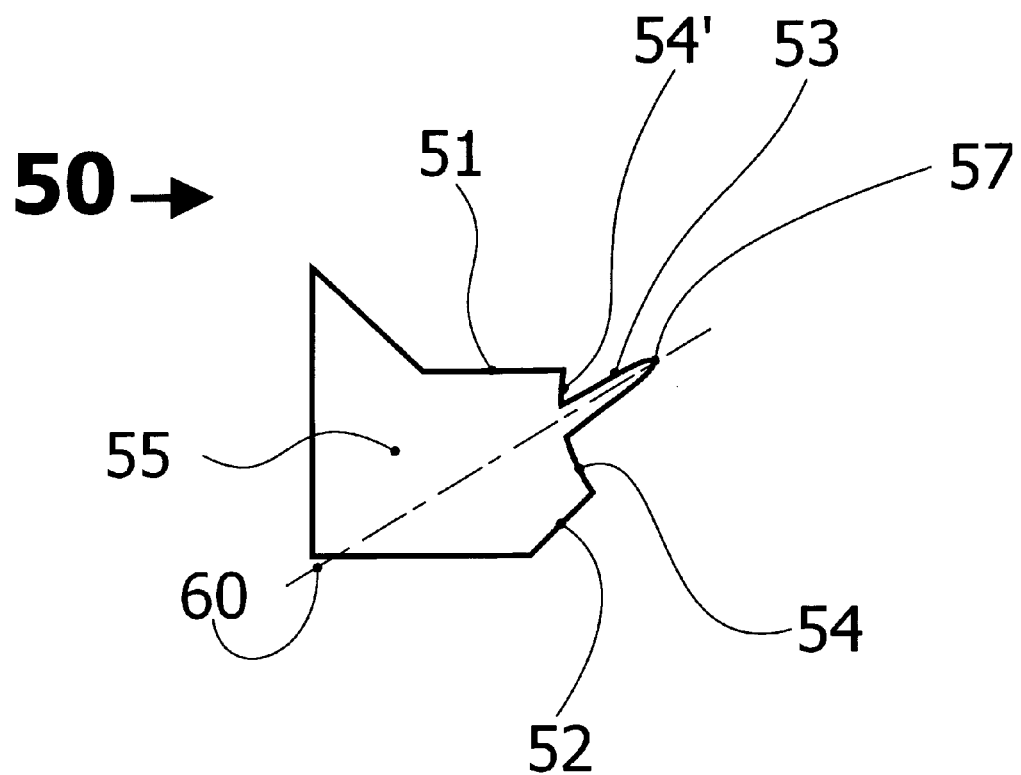
FIG. 4a shows another single press jaw according to the invention, with pressing shoulders at both sides of the penetrating segments.
Figure 4B:
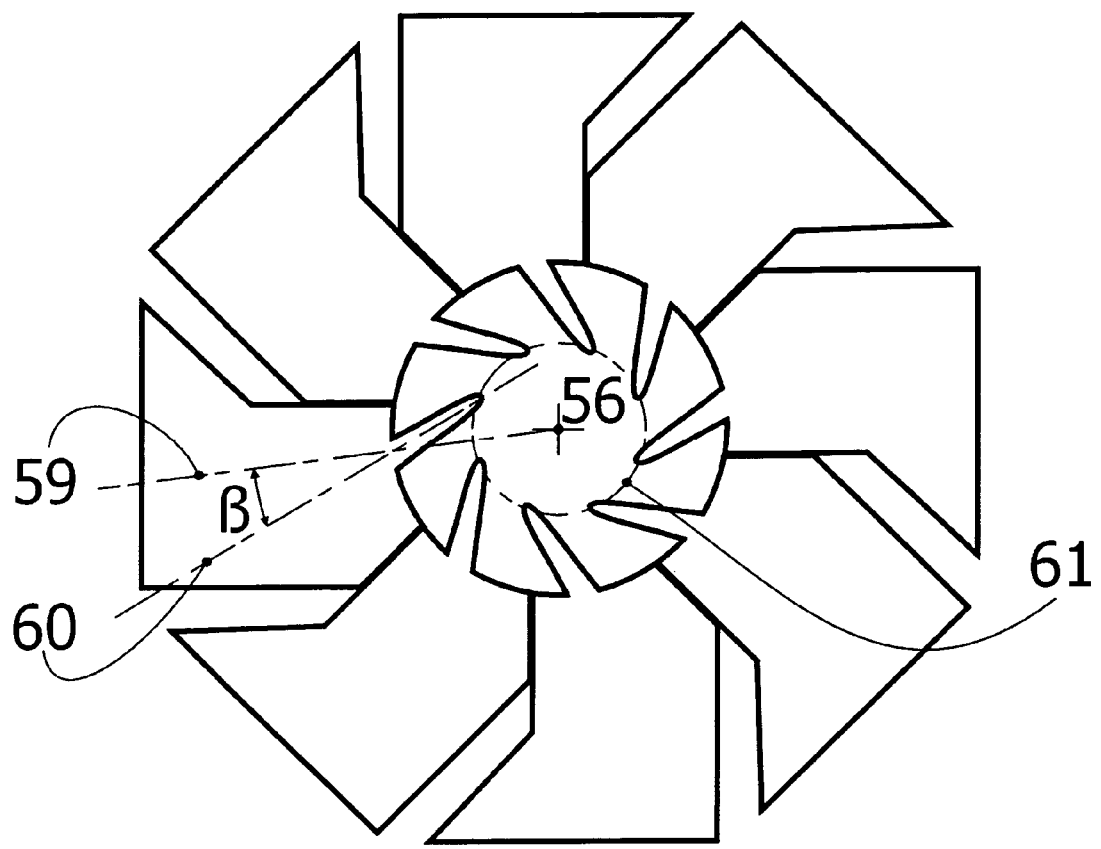
FIG. 4b shows a set of press jaws of FIG. 4a in a press according to the invention having penetrated the cylindrical tampon blank.

According to one aspect of the invention, a penetrating segment may be symmetrical along its length (from base to tip) as is shown, for example, in FIG. 4*a*, reference sign 53. Alternatively the penetrating segment may be asymmetric along its length, as depicted in FIG. 3*a*, reference sign 33, wherein one edge of the penetrating segment is straight and the other curved.

In FIGS. 3*a* and 3*b*, the pressing shoulders 34 are angular in the transversal direction in order to press the circumferential surface of the tampon blank into an essentially cylindrical form of smaller diameter.

In cross-section, the press jaws 30 each have penetrating segments 33 which have an asymmetrical shape (one edge straight and the other curved) in the direction running from the pressing head 35 to the extreme 38 of the penetrating segment, to form grooves in the longitudinal direction of the tampon blank. The medians 40 of the penetrating segments 33 have a curved shape.

FIG. 4*b* shows another embodiment of the press jaws of the apparatus of the present invention, in closed position, having penetrated a cylindrical tampon blank. The press of FIG. 4*b* comprises eight press jaws 50. These press jaws 50 are arranged in a star formation with respect to the press axis 56 and in particular at the same radial distance from the press axis 56. In their closed position, the press jaws 50 are supported on one another on their mutually opposite longitudinal sides 51 and 52.

One press jaw 50 comprises a penetrating segment 53 and pressing shoulders 54 and 54' arranged at both sides of the penetrating segment 53.

The penetrating segments 53 have an essentially symmetrical shape in the direction running from the pressing head 55 to the extreme 57 of the penetrating segment 53, in order to form grooves into the tampon blank.

The medians 60 of the penetrating segments 53 form an angle β of about ±15° with the radius 59 of the penetrating segments 53. The "radius of the penetrating segment", as used herein, refers to the straight radial line 59 running through the midpoint 56 of the fictive circle 61 formed by the extremes 57 of the penetrating segments 53, on the one hand, and the point where the median 60 of the penetrating segment 53 reaches the pressing head 55, on the other hand.

Figure 4C:
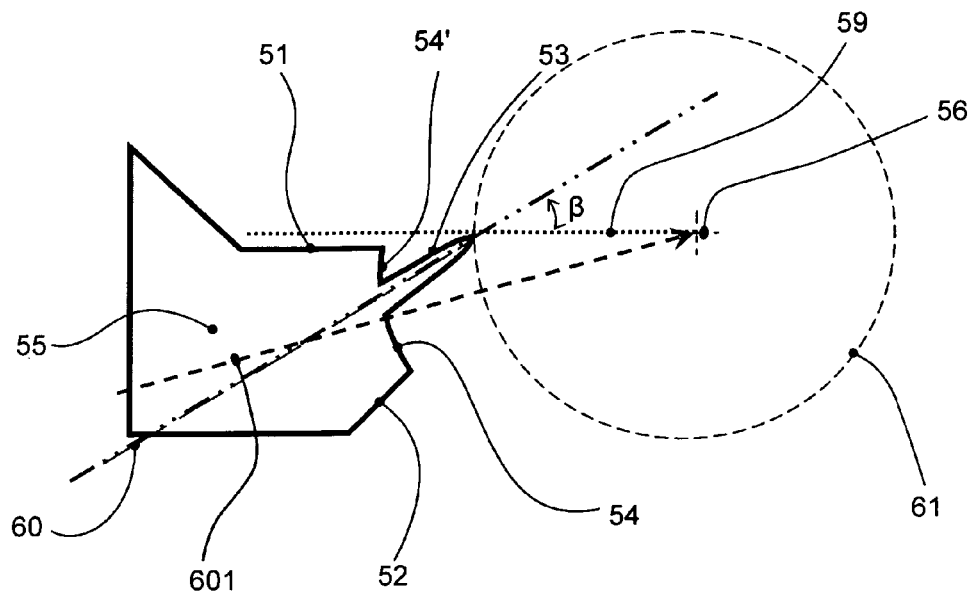
FIG. 4c shows a press jaw with a line of movement towards the press axis, and a median of the penetrating segment divergent from the line.

According to one embodiment of the invention, angle β is obtained by providing a press jaw comprising a penetrating segment (53) which median (60) diverges from the line of movement of the press jaw (601) as shown in FIG. 4c. The line (601) of movement of the press jaw essentially crosses the midpoint of the fictive circle (56) or press axis (37).

Figure 4D:
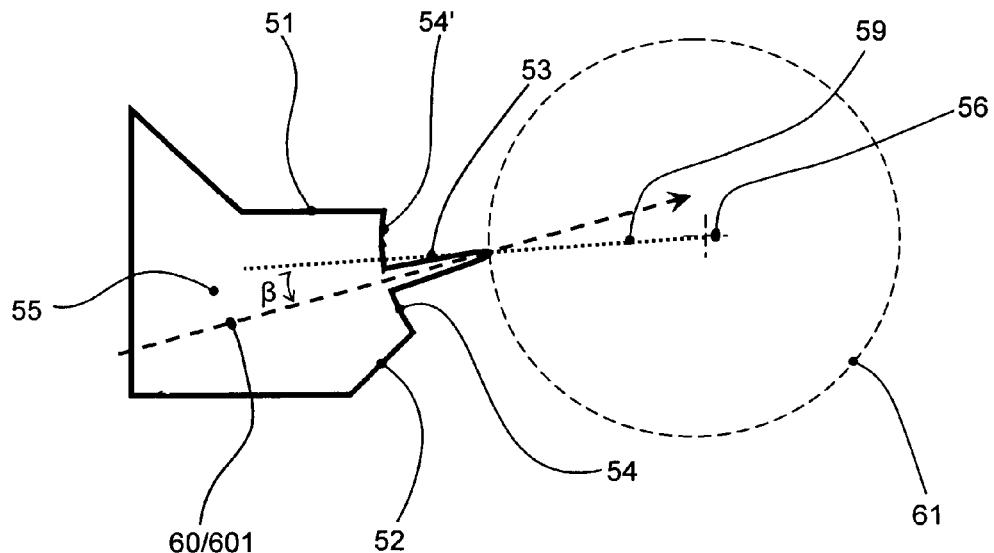
FIG. 4d shows a press jaw with a line of movement divergent from press axis, and a median of the penetrating segment parallel with the line.

According to another embodiment of the invention angle β is obtained by providing a press jaw comprising a penetrating segment (53) which median (60) is essentially parallel to the line of movement of the press jaw (601) as shown in FIG. 4d. The line (601) of movement of the press jaw essentially diverges from the midpoint of the fictive circle (56) or press axis (37). This allows a better distribution of the compression forces.

The pressing shoulders 54 have a curvature in the transversal direction in order to press the circumferential surface of the tampon blank into an essentially cylindrical form of smaller diameter.

The medians 60 of the penetrating segments 53 have an essentially straight shape in the longitudinal direction, to form essentially straight grooves in the axial direction (Y) of the tampon blank.

Figure 4E:
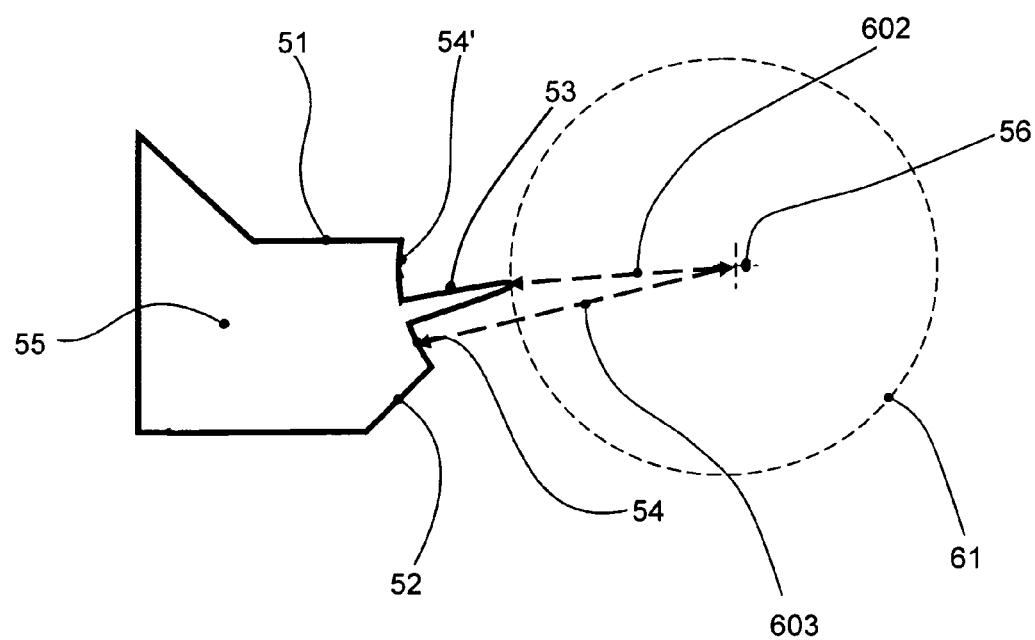
FIG. 4e shows a press jaw with indications measuring the impression depth.

According to one aspect of the invention, the radial distance 602 (FIG. 4e) between the midpoint 56 of the fictive circle 61 formed by the extremes 57 of the penetrating segments 53, and the extreme of a penetrating segment 57 and/or the radial distance 603 (FIG. 4e) between the midpoint 56 of the fictive circle 61 formed by the extremes 57 of the penetrating segments 53, and the pressing shoulder (54 or 54') is constant along the longitudinal axis of the press. Such measurement, indicative of the impression depth, is preferably taken when the jaws are in the closed position. A impression depth provides a tampon of constant diameter in the longitudinal direction such as, for example, in FIG. 1.

According to one aspect of the invention, the radial distance 602 between the midpoint 56 of the fictive circle 61 formed by the extremes 57 of the penetrating segments 53, and the extreme of a penetrating segment 57 and/or the radial distance 603 between the midpoint 56 of the fictive circle 61 formed by the extremes 57 of the penetrating segments 53, and the pressing shoulder (54 or 54') varies along the longitudinal axis. As already mentioned such measurement, indicative of the impression depth, is preferably taken when the jaws are in the closed position.

Variation in the impression depth along the longitudinal axis of the press allows tampons of different shapes to be formed. The shape is reflected in the longitudinal cross-section of a press, when the press jaws are closed. According to one aspect of the invention, said variation in impression depth provides a mushroom-shaped profile of a longitudinal cross-section of a press, when the press jaws are closed. Accordingly, the arrangement is capable of producing mushroom-shaped tampons (e.g. FIG. 1b). According to another aspect of the invention, said variation in impression depth provides a rivet-shaped profile of a longitudinal cross-section of a press, when the press jaws are closed. Accordingly, the arrangement is capable of producing rivet-shaped tampons. According to another aspect of the invention, said variation in impression depth provides a profile which has a dome head, a straight body and conical withdrawal end, when the press jaws are closed. Accordingly, the arrangement is capable of producing tampons with a domed insertion end and a conical withdrawal end (e.g. FIGS. 1c, 1d).

The invention further concerns a method for manufacturing the tampon of the invention. A strip of absorbent material having acceptable absorbency and modulus of elasticity properties that is capable of absorbing and/or retaining liquid, is wound up on itself to form an essentially cylindrical tampon blank.

In one embodiment, the essentially cylindrical blank is not surrounded by a covering, particularly when the blank tampon is made from cotton. In a preferred embodiment, the essentially cylindrical blank is at least partially surrounded by a covering. The covering is preferably not provided at the portion which will form the insertion end of the tampon. In order to improve the absorbing capacity and expansion capacity of the tampon, said covering is preferably a stretchable or elastic liquid-permeable covering.

The tampon can be provided with a withdrawal cord, according to any technique known in the art.

The tampon blank is pressed with the pressing apparatus described above. In order to form the ribs of the tampon, the method comprises compressing the tampon blank on its outer circumferential surface, forming longitudinal grooves and a fibre core. Preferably, the fibre core has a higher degree of compression from which less compressed longitudinal ribs extend outward. The degree of compression in the core is less than in tampons of the prior art, allowing the absorption of more liquid. The degree of compression can be controlled, depending on the angle of divergence of the median of groove or rib from the respective radii. Preferably, the tampon blank is compressed such that said longitudinal ribs extend outward at equal circumferential angle intervals.

In detail, a preferably cylindrical tampon blank is introduced in the press apparatus described above.

The tampon blank is radially compressed by press jaws, such as those described above. If the penetrating segments and the pressing shoulders are fixed to separate press jaws, the tampon blank may be first pressed with the penetrating segments and subsequently with the pressing shoulders. Alternatively, the penetrating segments and the pressing shoulders may press the tampon blank simultaneously. The latter will obviously be the case when the penetrating segments and pressing shoulders are fixed to the same press jaws. In the press, the tampon blank is preferably compressed in a single pressing operation by the penetrating segments and pressing shoulders simultaneously.

The penetrating segments will preferably press the tampon blank on strips of the circumferential surface which are narrower than the strips of the circumferential surface pressed by the pressing shoulders. Preferably also, the strips pressed by the penetrating segments have an equal length and width and the strips pressed by the pressing shoulders also have an equal length and width. In this way, ribs are formed, defined by longitudinal grooves on a solid fibre core. The pressing shoulders will press on the circumference of the so formed ribs in order to obtain an essentially cylindrical form with a smaller diameter. The memory effect of the tampon blank maintains the shape of the compressed tampon form.

Figure 5:
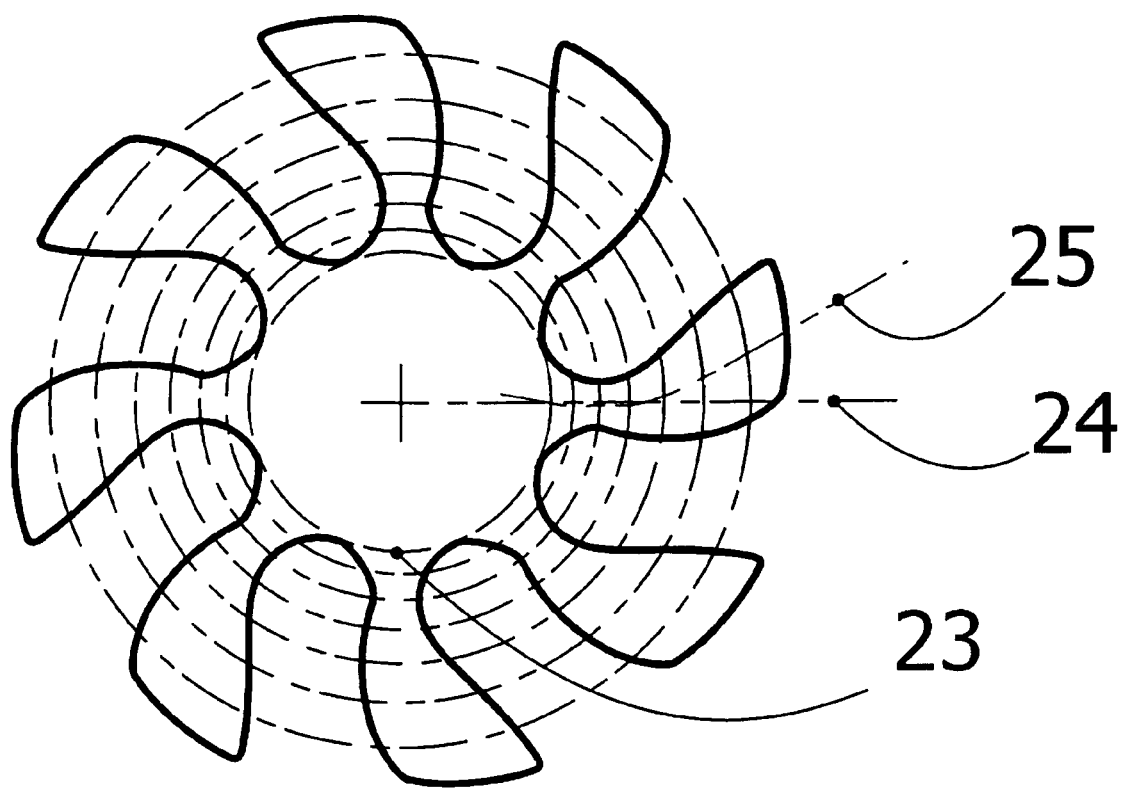
FIG. 5 illustrates schematically a preform formed according to a method or using a press according to the invention.
Figure 6:
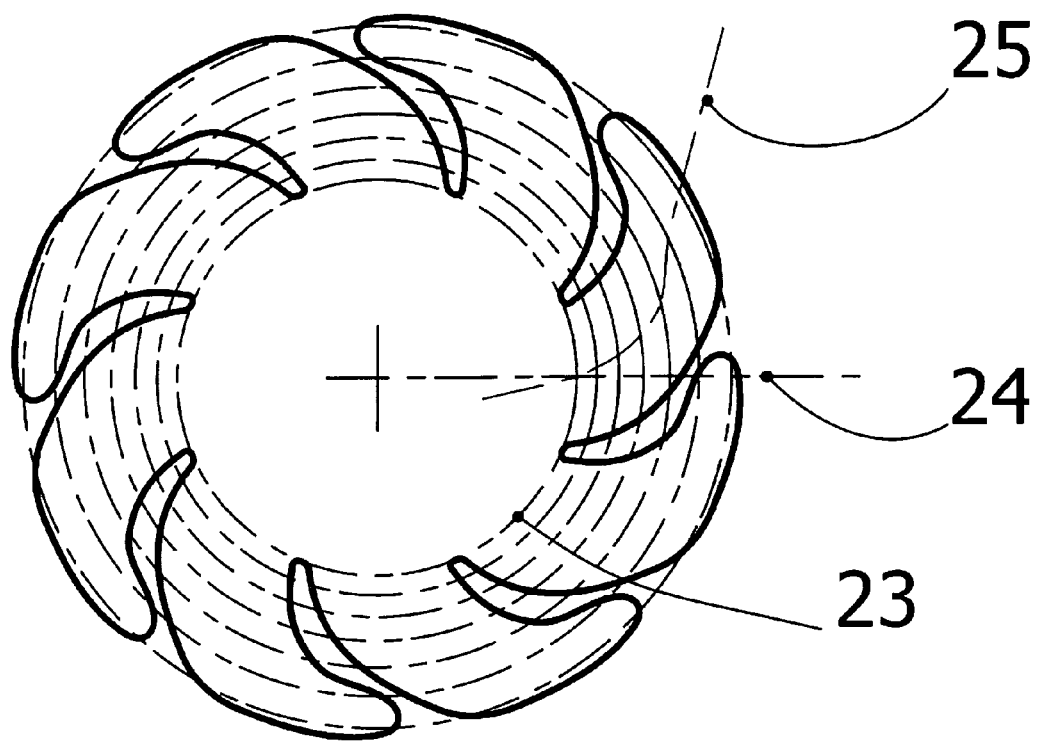
FIGS. 6 to 8 illustrate schematically various rib-patterns of cross-sections along the X-X axis of tampons according to the invention.
Figure 7:
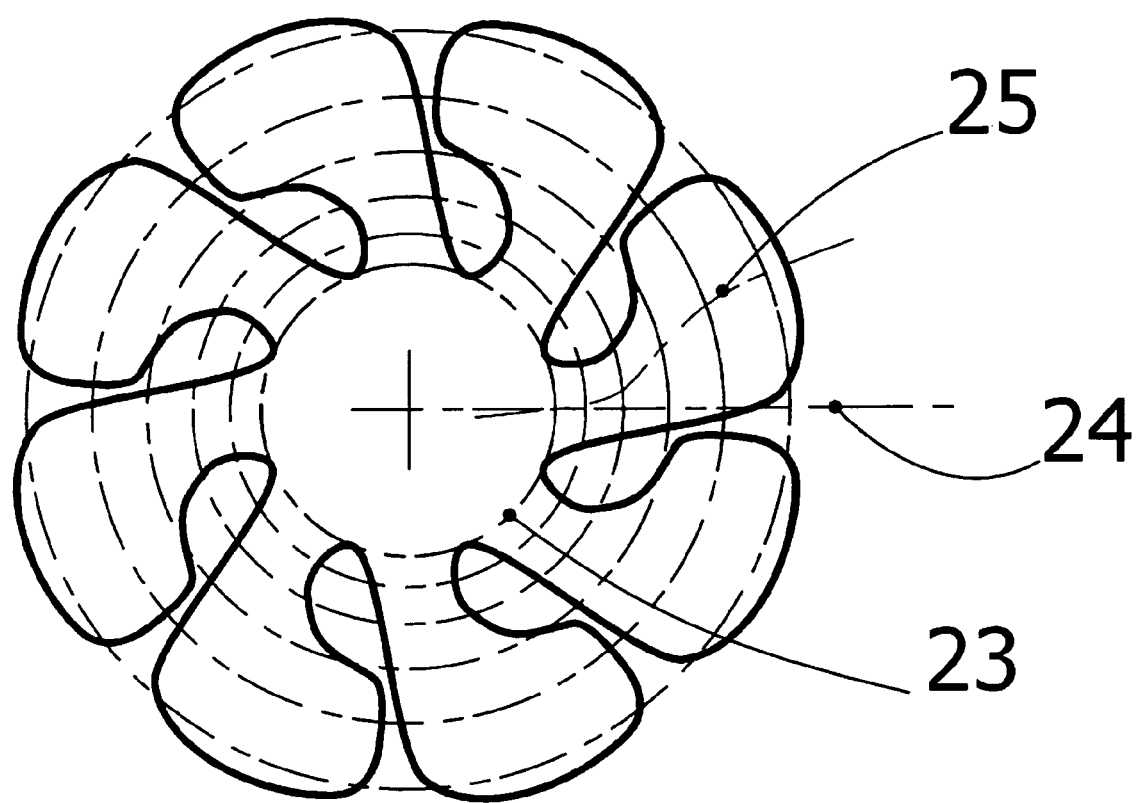

The tampon blank, having been pressed by the penetrating segments and pressing shoulders, forms a preform which is ejected from the press. This preform is simultaneously subjected to final shaping downstream. This final shaping includes a radial pressure being exerted on the total circumference of the preform. This radial pressure has the effect that the adjacent longitudinal ribs are pressed against one another, so that the grooves are substantially closed and the circumferential surface of the tampon is substantially smooth and soft. An example of a preform formed by the press of the invention is schematically depicted in FIG. 5.

The tampon blank is, depending on the properties of the fibrous material used, in particular in the event of use being made of highly expansive fibres of irregular cross section with a strong memory effect, pressed at a temperature of the press jaws to the final shape of the tampon, in order to achieve the desired dimensional stability of the fibrous material by eliminating the memory effect of the fibres, which immediately becomes effective again on contact with bodily fluid and thus increases the expansion and absorption speed of the tampon with the least possible use of fibrous material.

It is apparent that there has been provided in accordance with the invention, a tampon that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

What is claimed is:

1. A tampon, having essentially a cylindrical shape, comprising:
    a generally cylindrical compressed fiber body formed as a regular pattern of at least three longitudinal ribs;
    wherein the final compression of the fiber body is non-radial;
    wherein all of the provided ribs have proximal ends attached to the body that extend outward to distal ends of said ribs;
    wherein all of the provided ribs, in transverse cross-section, have a median at least partially diverging from the radius in a same direction and at an angle of at least 10 degrees along at least a portion of the median;
    wherein the medians of all the provided ribs diverge in either a clockwise direction for all of said ribs or in a counter-clockwise direction for all of said ribs;
    the median of each of said ribs is at an angle between 10° and 20° or between −10° and −20° vis á vis the radius of the same rib; and
    the medians of all the provided ribs diverge at substantially the same angle.

2. The tampon according to claim 1, in which said median has a curved shape.

3. The tampon according to claim 1, in which said median has an angular shape.

4. The tampon according to claim 1, in which said median has a straight shape.

5. The tampon according to claim 1, in which the tampon is provided with a finger recess.

6. The tampon according to claim 1, in which the tampon is provided with a dome shaped insertion end.

7. The tampon according to claim 1, in which the tampon is mushroom shaped.

8. The tampon according to claim 1, in which the tampon is rivet shaped.

9. The tampon according to claim 1, in which the tampon is provided with a conical shaped withdrawal end.

10. The tampon according to claim 1, in which the tampon is provided with a withdrawal cord.

11. The tampon according to claim 1, in which the ribs touch each other so as to form an essentially smooth cylindrical outer surface.

12. The tampon according to claim 1 provided with one or more markings on the surface.

13. The tampon according to claim 12 wherein said marking comprises one or more of alpha numerals, graphic illustrations, patterns, solid colors or photographic illustrations.

14. The tampon according to claim 12 wherein said marking is information.

15. The tampon according to claim 1 provided with one or more chemical indicators that are capable of changing color.

16. The tampon according to claim 15 wherein a chemical indicator is capable of color change according to the presence of a disease or condition detectable by a color change reaction.

17. The tampon according to claim 16 wherein a condition is anemia and a chemical indicator detects iron or hemoglobin.

18. The tampon according to claim 16 wherein a condition is diabetes and a chemical indicator detects glucose.

19. The tampon according to claim 16 wherein a condition is a sexually transmitted disease and a chemical indicator detects antigens towards said sexually transmitted disease.

20. A tampon, having essentially a cylindrical shape, comprising:
    a generally cylindrical compressed fiber body formed as a regular pattern of at least three longitudinal grooves;
    wherein the final compression of the fiber body is non-radial;
    wherein all of the provided grooves extend from the outer surface of the tampon toward a core;
    wherein all of the provided grooves have a bottom proximate to the core;
    wherein all of the provided grooves, in transverse cross-section, have a median at least partially diverging from the radius in a same direction and at an angle of at least 10 degrees along at least a portion of the median;
    wherein the medians of all the provided grooves diverge in either a clockwise direction for all of said grooves or in a counter-clockwise direction for all of said grooves;
    the median of each of said grooves is at an angle between 10° and 20° or between −10° and −20° vis á vis the radius of the same groove; and
    the medians of all the provided grooves diverge at substantially the same angle.

* * * * *